(12) United States Patent
Abbott et al.

(10) Patent No.: US 6,277,489 B1
(45) Date of Patent: Aug. 21, 2001

(54) SUPPORT FOR HIGH PERFORMANCE AFFINITY CHROMATOGRAPHY AND OTHER USES

(75) Inventors: Nicholas Abbott, Madison, WI (US); Pieter Stroeve, Davis, CA (US); Timothy B. Dubrovsky, Flemington, NJ (US); Zhizhong Hou, Davis, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 09/205,750

(22) Filed: Dec. 4, 1998

(51) Int. Cl.$^7$ ............................................. B32B 5/16
(52) U.S. Cl. .................. 428/403; 427/217; 427/220; 428/404; 428/407; 428/450; 428/457; 428/699; 428/701; 428/702; 435/7.1; 435/7.7; 435/7.8; 435/287.1; 435/287.2; 435/287.9
(58) Field of Search .................. 428/403, 404, 428/407, 450, 457, 699, 701, 702; 427/2.11, 2.14, 217, 220; 435/7.1, 7.7, 7.8, 7.9, 287.1, 287.2, 287.9; 436/72, 73, 120, 127, 80, 501; 514/495, 499, 501, 706, 770

(56) References Cited

U.S. PATENT DOCUMENTS

| | | | |
|---|---|---|---|
| 4,931,498 | * | 6/1990 | Pidgeon .......................... 525/54.1 |
| 4,944,985 | | 7/1990 | Alexander et al. . |
| 5,196,267 | | 3/1993 | Barder et al. . |
| 5,217,866 | | 6/1993 | Summerton et al. . |
| 5,472,881 | * | 12/1995 | Beebe et al. ........................ 436/94 |
| 5,491,097 | | 2/1996 | Ribi et al. . |
| 5,501,875 | | 3/1996 | Loboda et al. . |
| 5,620,850 | | 4/1997 | Bamdad et al. . |
| 5,693,152 | | 12/1997 | Carron . |
| 5,728,431 | * | 3/1998 | Bergbreiter et al. ............. 427/388.1 |
| 5,919,576 | * | 7/1999 | Hui et al. .......................... 428/545 |
| 5,942,397 | * | 8/1999 | Tarlov et al. ......................... 435/6 |
| 5,955,365 | | 11/1999 | Szoka, Jr. et al. . |
| 5,977,084 | | 9/1999 | Szoka, Jr. et al. . |
| 6,013,855 | * | 1/2000 | McPherson et al. ................ 623/11 |

OTHER PUBLICATIONS

Spinke et al., "Molecular Recognition at Self–Assembled Monolayers: The Construction of Multicomponent Multi-layers" *Langumuir* 9:1821–1825 (1993).

Lenk et al., "Structural Investigation of Molecular Organization in Self–Assembled Monolayers of a Semifluorinated Amidethiol" *Langmuir* 10:4610–4617 (1994).

Drawhorn et al., "Anchoring of Nematic Liquid Crystals on Self–Assembled Monolayers Formed from Alkanethiols on Semitransparent Films of Gold" *J. Phys. Chem.* 99:16511 (1995).

Brust et al., "Synthesis of Thiol–derivatised Gold Nanoparticles in a Two–phase Liquid–Liquid System" *J. Chem. Soc. Chem. Commun.* pp. 801–802 (1994).

Johnson et al., "Alkanethiol Molecules Containing an Aromatic Moiety Self–Assembled onto Gold Clusters" *Langmuir* 13:51–57 (1997).

(List continued on next page.)

*Primary Examiner*—Hoa T. Le
(74) *Attorney, Agent, or Firm*—Townsend and Townsend and Crew LLP

(57) ABSTRACT

Multilayered particulate materials are formed by coating a particulate substrate with a metal and adsorbing an organic layer comprising a recognition moiety onto the metal film. The recognition moiety interacts with an analyte of interest allowing for its detection, purification, etc. Suitable recognition moieties can be selected from a range of species including, small molecules, polymers and biomolecules and the like. The novel particulate materials of the invention can be utilized in an array of methods including, ion-exchange, ion-selective ion-exchange, assays, affinity dialysis, size exclusion dialysis, as supports in solid phase synthesis, combinatorial synthesis and screening of compound libraries and the like.

44 Claims, 2 Drawing Sheets

OTHER PUBLICATIONS

Green et al., "Three–Dimensional Monolayers: nanometer-Sized Electrodes of Alkanethiolate–Stabilized Gold Cluster Molecules" *J. Phys. Chem.* 101:2663–2668 (1997).

Grabar et al., "Nanoscale Characterization of Gold Colloid Monolayers: A Comparison of Four Techniques" *Anal. Chem.* 69:471–477 (1997).

Grabar et al., "Two–Dimensional Arrays of Colloidal Gold Particles: A Flexible Approach to Macroscopic Metal Surfaces" *Langmuir* 12:2353–2361 (1996).

Welsch et al., "Silanol effects in reversed–phase liquid chromatography" *J. Chromatogr.* 506:97–108 (1990).

Kohler et al., "Comprehensive Characterization of Some Silica–Based Stationary Phases for High–Performance Liquid Chromatography" *J. Chromatogr.* 352:275–305 (1986).

Tuel et al., "A $^{29}$Si NMR Study of the Silanol Population at the Surface of Derivatized Silica" *Langmuir* 6:770–775 (1990).

Sagiv, "Organized Monolayers by Adsorption. 1. Formation and Structure of Oleophobic Mixed Monolayers on Solid Surfaces" *J. Am. Chem. Soc.* 102:92–98 (1980).

Xia et al., "Microcontact Printing of Octadecylsiloxane on the Surface of Silicon Dioxide and Its Application in Microfabrication" *J. Am. Chem. Soc.*, 117:9576–9577 (1995).

Netzer et al., "Adsorbed Monolayers Versus Langmuir-Blodgett Monolayers—Why and How? II: Characterization of Built–Up Films Constructed by Stepwise Adsorption of Individual Monolayers" *Thin Solid Films* 100:67–76 (1983).

Frey et al., "Covalent Attachment and Derivatization of Poly(L–lysine) Monolayers on Gold Surfaces As Characterized by Polarization—Modulation FT–IR Spectoscopy" *Anal. Chem.* 68:3187–3193 (1996).

Menon, et al., "Fabrication and Evaluation of Nanoelectrode Ensembles" *Anal. Chem.* 67:1920–1928 (1995).

Koura N., "Chapter 17:Electroless Plating of Silver," *In: Electroless Plating: Fundamentals and Applications*, Ed. Mallory, G.O. et al., American Electroplaters and Surface Finishers Society, Orlando (1990).

Hou, Z. et al., "Electroless Gold as a Substrate for Self–Assembled Monolayers" *Langmuir* 14:3287–3297 (1998).

* cited by examiner

SUPPORT FOR HIGH PERFORMANCE AFFINITY CHROMATOGRAPHY AND OTHER USES

CROSS-REFERENCE TO RELATED APPLICATIONS

This application is related to U.S. patent application Ser. No. 09/206,084, filed on an even day herewith (Dec. 4, 1998), the teachings of which are incorporated herein by reference for all purposes.

STATEMENT AS TO RIGHTS TO INVENTIONS MADE UNDER FEDERALLY SPONSORED RESEARCH AND DEVELOPMENT

This work was partially supported by the National Science Foundation MRSEC Program, (DMR-9400354) and the CAREER Program (CTS-9410147). Support was also received from the Office of Naval Research, Presidential Early Career Award for Science and Engineering (N00014-97-1-0703).

BACKGROUND OF THE INVENTION

Self-assembled monolayers formed by the chemisorption of alkanethiols on gold are likely to now be the most intensively characterized synthetic organic monolayers prepared to date. See, Ulman, AN INTRODUCTION TO ULTRATHIN ORGANIC FILMS: FROM LANGMUIR-BLODGETT TO SELF ASSEMBLY, Academic Press, San Diego, 1991; Dubois el al., *Annu. Rev. Phys. Chem.*, 43: 437 (1992). These monolayers form spontaneously during immersion of evaporated films of gold in solutions of alkanethiols as a result of chemisorption of sulfur on the (111) textured surface of the films. The molecules self-organize into a commensurate $\sqrt{3}\times\sqrt{3}R30°$ lattice on the surface of the Au(111). See, Porter, *J. Am. Chem. Soc.*, 109: 3559 (1987); Camillone III, et al., *Chem. Phys.*, 98: 3503 (1993); Fenter et al., *Science*, 266: 1216 (1994); 20; Chidsey et al., *Langmuir*, 6: 682 (1990); Sun etal., *Thin Solid Films*, 242: 106 (1994). For monolayers formed from $CH_3(CH_2)_nSH$, n>9, at least, the aliphatic chains of the monolayers are extended in the all-trans conformation and tilted approximately 30° from the normal of the surface. Because the spacing between sulfur groups on the $\sqrt{3}\times\sqrt{3}R30°$ lattice is, on average, 4.9 Å, whereas the van der Waals diameter of an aliphatic chains is only ~4 Å, the aliphatic chains within these SAMs tilt from the normal so as to come into van der Waals contact and thereby maximize their cohesive dispersive interactions. Studies of the lateral structure within monolayers using X-ray diffraction reveal the existence of domains of size ~100 Å, where each domain has one of six different tilt directions relative to the Au(111) face. See, Fenter et al., *Science*, 266: 1216 (1994). Recent studies have shown the existence a c(4×2) superlattice, the cause of which remains unresolved.

Self-assembled monolayers formed with ω-substituted alkanethiols on the surface of gold have been used as model surfaces in a number of past studies of the interactions of proteins with surfaces (Spinke et al., *Langumuir*, 9: 1821 (1993); Willner et al., *J. Am. Chem. Soc.*, 114: 10965 (1992); Song et al., *J. Phys, Chem.*, 97: 6564 (1993); Mrksich et al., *J. Am. Chem. Soc.*, 117: 12009 (1995)). For example, multilayer systems based on biotinylated alkanethiols and streptavidin have been used in schemes for the immobilization of Fab fragments of antibodies on surfaces (Spinke et al, *Langumuir*, 9: 1821 (1993)), and SAMs formed from NHS-activated disulfides have been used to form enzyme-based electrodes by covalent immobilization of glutathione reductase (Willner et al., *J. Am. Chem. Soc.*, 114: 10965 (1992)). Cytochrome c, when adsorbed to SAMs formed from mercaptoundecanoic acid, has also been shown to be active and to possess a formal potential nearly identical to that of cytochrome c bound to physiological membranes (Song et al., *J. Phys, Chem.*, 97: 6564 (1993)).

Whereas, investigations such as those described above have firmly established the use of SAMs for studies of specific interactions between proteins and surfaces, mixed SAMs formed from hydrophobic (methyl-terminated) and hydrophilic (hydroxyl-, oligo(ethylene glycol)-terminated) alkanethiols have also been used as model surfaces in studies of non-specific adsorption of proteins onto surfaces. Whitesides and coworkers, for example, have reported a study of the non-specific adsorption of fibrinogen, lysozyme, pyruvate kinase and RNAse to mixed SAMs (Prime et al., *J. Am. Chem. Soc.*, 115: 10714 (1993); Prime et al., *Science*, 252: 1164 (1991)). By using ellipsometry, SAMs formed from oligo(ethylene glycol)-terminated alkanethiols were shown to resist irreversible adsorption of these proteins.

Surfaces prepared by the chemisorption of organosulfur compounds on evaporated films of gold are not limited to the alkanethiols. Self-assembled monolayers formed from perfluorinated organosulfur compounds have also been reported. See, Lenk et al., *Langmuir*, 10: 4610(1994); Drawhorn et al., *J. Phys. Chem.*, 99: 16511 (1995). These surfaces, too, can be highly ordered, although, interestingly, the origin of the order within the monolayer is largely intramolecular and contrasts, therefore, to monolayers formed from alkanethiols (where the order largely reflects the cohesive intermolecular dispersion force). Steric interactions between adjacent fluorine atoms of a perfluorinated chain cause the chain to twists itself into a rigid, helical conformation. That is, an isolated perfluoro chain is stiff, as compared to an aliphatic chain. Because perfluorinated chains have larger cross-sectional areas than alkanethiols, monolayers formed on gold from perfluorinated thiols are not tilted from the normal to the same degree as alkanethiols. See, Drawhorn et al., *J. Phys. Chem.*, 99: 16511 (1995). Estimates by IR studies place the tilt of the perfluorinated chains at 0~10°. Because perfluorinated chains within SAMs on Au(111) are not tilted to the same degree as the alkanethiols, their surfaces are not expected to possess domains formed from regions of monolayer with different tilt directions (as occurs with monolayers formed from alkanethiols).

Past studies of the interactions of proteins and SAMs formed from alkanethiols on gold have used either planar surfaces prepared by electron-beam or thermal deposition of gold. See, for example, Prime et al., *Science*, 252: 1164 (1991); Prime et al., *Science*, 252: 1164 (1991) or highly curved surfaces formed by using colloidal gold (Brust et al., *J. Chem. Soc. Chem. Commun.*, 1994: 801 (1994); Johnson et al., *Langmuir*, 13: 51 (1997); Green et al., *J. Phys. Chem.*, 101: 2663 (1997); Natan et al., *Anal. Chem.*, 69: 471 (1997); Grabar et al., *Langmuir*, 12: 2353 (1996); Hancock, HIGH PERFORMANCE LIQUID CHROMATOGRAPHY IN BIOTECHNOLOGY, Wiley, New York (1990)).

Whereas planar interfaces prepared by the evaporation of gold have surface areas that are too small to be generally useful for biological assays based on measurements of bulk concentrations of analytes, colloidal particles (~1–10 nm in size) are not large enough to pack (unsupported) in columns through which reagents can be readily passed. Due to the expense of the materials involved, the use of larger gold particles is not practical.

Various electroless plating techniques have been used to coat particles with layers of various metals. For example, Barder et al., U.S. Pat. No. 5,196,267, discloses silica microspheres having a diameter of about 0.1 µm to about 10 µm provided with a thin surface layer of a metal. The silica particles are contacted with an aqueous or alcoholic solution of a metal compound to deposit the surface layer. Moreover, Alexander et al., U.S. Pat. No. 4,944,985 discloses a process for the electroless plating of easily reducible metals onto ultrafine, usually inert particles. Neither of these references teaches forming an organic layer on the metal film.

Self assembled monolayers have been constructed on silica particles by a number of known methods, however, silica gel particles are a less than ideal substrate for a number of reasons.

First, the surface of silica is formed from silanol (Si—OH) and siloxane (Si—O—Si groups). The surface concentration of silanol groups typically ranges between 1–3 µmol/m$^2$ (Welsch et al., *J. Chromatogr.*, 506: 97 (1990), Kohler et al., *J. Chromatogr.*, 352: 275 (1986)). Fully hydroxylated silica can have an areal density of silanol groups as high as 8 µmol/m$^2$ (Tuel et al., *Langmuir*, 6: 770 (1990)). Because some fraction of these silanol groups are deprotonated at physiological pHs, the surface of silica gel presents a net negative charge under solution conditions that are not highly acidic. Electrostatic interactions between these surface-bound charges and proteins are one principal cause of non-specific adsorption of proteins onto silica gel (Hancock, HIGH PERFORMANCE LIQUID CHROMATOGRAPHY IN BIOTECHNOLOGY, Wiley, New York, 1990).

The second disadvantage of silica gel-based supports is that chemical modification of the surface of silica gel generally requires the use of silane-based chemistries (Sagiv, *J. Am. Chem. Soc.*, 102: 92 (1980)). Although monomolecular layers of alkyltrichlorosilanes have been reported to form on silicon oxide surfaces (Xia et al., *J. Am. Chem. Soc.*, 117: 9576 (1995)), reproducible preparation of such monolayers is a substantial challenge. For example, Netzer and coworkers have reported surface coverages of vinyl-terminated alkyltrichlorosilane to be approximately 63% of that of a densely-packed monolayer (Netzer et al., *This Solid Films*, 100: 67 (1983)). Also, Sagiv and coworkers have suggested that incomplete monolayers formed from alkyltrichlorosilanes have a heterogeneous island-like structure (Maoz et al., *J. Colloid and Interf Sci.*, 100: 465 (1984); Cohen et al., *J. Chem Phys.*, 90: 3054 (1986)). In contrast, Whitesides and coworkers have concluded that incomplete monolayers formed from alkyltrichlorosilanes are homogenous and disordered. (Wasserman et al., *J. Am. Chem. Soc.*, 111: 5852 (1989); Tidswell et al, *Phys. Rev. B.*, 41: 1111 (1990) and Ulman, AN INTRODUCTION TO ULTRATHIN ORGANIC FILMS: FROM LANGMUIR-BLODGETT TO SELF-ASSEMBLY, Academic Press, Boston, 1991).

Thus, a method of preparing a particulate material having a substantially homogeneous, easily assembled organic layer that does not adventitiously and/or nonspecifically bind charged species would represent a significant advance in the art. Surprisingly, the present invention provides such particles, and methods of preparing and using these particles.

SUMMARY OF THE INVENTION

It has now been discovered that solution-phase methods can be used to coat micrometer-sized, silica particles with polycrystalline metal films, particularly gold films. The metal coated silica particles can be functionalized with SAMs (mixed and homogeneous) formed from substituted organosulfur molecules. Because a wide range of functional groups can be easily introduced onto surfaces by these methods, these materials are useful as synthesis supports and for a range of purification methods and assays.

The multilayered particles are useful as synthesis supports for assembling a variety of molecules by solid phase synthetic techniques. Additionally, the particles can be used to both synthesize and screen combinatorial libraries and microarrays of diverse molecules. The particles of the invention can be used in purification strategies such as size exclusion chromatography and affinity chromatography, and in a number of assays, such as competitive, non-competitive and sandwich assays. Moreover, the particles can be used as a free-flowing powder. Alternatively, the particles can be adsorbed onto a plate or other substrate to form a device analogous to a thin layer chromatography plate. Further, the particles can be compressed or molded to form a component of a monolithic structure. The particles can also be incorporated into an aerogel.

Thus, in a first aspect, the invention provides a multilayered material comprising:

a particulate substrate;

a metal film layered onto the substrate; and an organic layer attached to the metal film.

In a second aspect, the invention provides a multilayered material comprising:

a silica substrate;

a metal film layered onto the substrate;

an organic layer attached to the metal film; and a recognition moiety attached to a member selected from the group consisting of the organic layer, the metal film and combinations thereof.

In a third aspect, the present invention provides a multilayered material comprising:

a silica substrate;

a metal film layered onto the substrate;

an organosulfur layer attached to the metal film; and a recognition moiety attached to the organosulfur layer.

In a fourth aspect, the present invention provides a method for capturing a molecule comprising:

contacting the molecule with the multilayered material comprising;

a particulate substrate;

a metal film layered onto the substrate;

an organic layer attached to the metal film; and a recognition moiety attached to a member selected from the group consisting of the organic layer, the metal film and combinations thereof, wherein the recognition moiety associates with the molecule forming a multilayered material-molecule complex, thereby capturing the molecule.

In a fifth aspect, the invention provides a device for capturing a molecule comprising:

a multilayered material comprising;

a particulate substrate;

a metal film layered onto the substrate;

an organic layer attached to the metal film; and a recognition moiety attached to a member selected from the group consisting of the organic layer, the metal film and combinations thereof, wherein the recognition moiety associates with the molecule forming a multilayered material-molecule complex, thereby capturing the molecule; and a means to contain the multilayered material.

In a sixth aspect, the present invention provides a method for isolating a molecule from other molecules by affinity chromatography comprising:
(a) contacting the molecule with a plurality of multilayered particles, the particles comprising;
a particulate substrate;
a metal film layered onto the substrate;
an organic layer attached to the metal film; and
a recognition moiety attached to a member selected from the group consisting of the organic layer, the metal film and combinations thereof;
(b) forming a complex between the recognition moiety and the molecule, thereby forming a plurality of particle-molecule complexes; and
(c) washing the plurality of particle-molecule complexes with a solvent for the other molecules.

In a seventh aspect, the invention provides a method of isolating a first molecule from a second molecule by size exclusion chromatography, comprising:
(a) contacting the first and second molecule with a plurality of multilayered particles to form a mixture comprising the first molecule, the second molecule and theparticles, the particles comprising;
a particulate substrate;
a metal film layered onto the substrate;
a hydrophilic polymer attached to the metal film; and
(b) contacting the mixture with a solvent for both the first molecule and the second molecule.

In an eighth aspect, the present invention provides a method for determining the presence or amount of an analyte in a test sample comprising:
(a) contacting the test sample with a plurality of multilayered particles, the particles comprising;
a particulate substrate;
a metal film layered onto the substrate;
an organic layer attached to the metal film; and
a recognition moiety attached to a member selected from the group consisting of the organic layer, the metal film and combinations thereof;
(b) forming a complex between the recognition moiety and at least a portion of the analyte, thereby forming a plurality of particle-analyte complexes; and
(c) detecting the analyte.

In an ninth aspect, the present invention provides a method of detecting or quantifying binding affinity between a first binding partner and a member selected from the group consisting of a recognition moiety, a second binding partner and combinations thereof, the method comprising:
(a) contacting a member selected from the group consisting of the first binding partner and a first binding partner-second binding partner complex with a plurality of multilayered particles, the particles comprising;
a particulate substrate;
a metal film layered onto the substrate;
an organic layer attached to the metal film; and
a recognition moiety attached to a member selected from the group consisting of the organic layer, the metal film and combinations thereof;
(b) forming a plurality of particle-first binding partner complexes; and
(c) measuring the affinity.

In a tenth aspect, the present invention provides a method of producing a multilayered particle comprising:
(a) contacting a particulate substrate with a metal plating solution to form a particle having a metal film layered thereon;
(b) contacting the particle having a metal film layered thereon with a plurality of organic molecules that associate with the metal film.

In an eleventh aspect, the present invention provides a method for assembling a compound, comprising:
(a) adding a first component of the compound to a multilayered material comprising;
a particulate substrate;
a metal film layered onto the substrate;
an organic layer attached to the metal film;
(b) adding a second component of the compound to the multilayered material; and
(c) reacting the first component and the second component to form a first product.

Other objects and advantages of the present invention will be apparent from the detailed description and examples that follow.

DETAILED DESCRIPTION OF THE INVENTION AND THE PREFERRED EMBODIMENTS

Abbreviations and Definitions

Figure 1:
FIG. 1 is a scanning electron micrograph of electroless gold deposited onto the surface of silica gel. The image was formed by back-scattered electrons. The scale bar corresponds to 2 $\mu$m.

SAM, self assembled monolayer.

The term "attached," as used herein encompasses interactions including, but not limited to, covalent bonding, ionic bonding, chemisorption, physisorption and combinations thereof.

The term "independently selected" is used herein to indicate that the groups so described can be identical or different The term "alkyl" is used herein to refer to a branched or unbranched, saturated or unsaturated, monovalent hydrocarbon radical having from 1–30 carbons and preferably, from 4–20 carbons and more preferably from 6–18 carbons. When the alkyl group has from 1–6 carbon atoms, it is referred to as a "lower alkyl." Suitable alkyl radicals include, for example, structures containing one or more methylene, methine and/or methyne groups. Branched structures have a branching motif similar to i-propyl, t-butyl, i-butyl, 2-ethylpropyl, etc. As used herein, the term encompasses "substituted alkyls."

"Substituted alkyl" refers to alkyl as just described including one or more functional groups such as lower alkyl, aryl, acyl, halogen (i.e., alkylhalos, e.g., $CF_3$), hydroxy, amino, alkoxy, alkylamino, acylamino, thioamido, acyloxy, aryloxy, aryloxyalkyl, mercapto, thia, aza, oxo, both saturated and unsaturated cyclic hydrocarbons, heterocycles and the like. These groups may be attached to any carbon of the alkyl moiety. Additionally, these groups may be pendent from, or integral to, the alkyl chain.

The term "aryl" is used herein to refer to an aromatic substituent which may be a single aromatic ring or multiple aromatic rings which are fused together, linked covalently, or linked to a common group such as a methylene or ethylene moiety. The common linking group may also be a carbonyl as in benzophenone. The aromatic ring(s) may include phenyl, naphthyl, biphenyl, diphenylmethyl and benzophenone among others. The term "aryl" encompasses "arylalkyl."

The term "arylalkyl" is used herein to refer to a subset of "aryl" in which the aryl group is attached to the nucleus shown in Formulae 1–4 by an alkyl group as defined herein.

"Substituted aryl" refers to aryl as just described including one or more functional groups such as lower alkyl, acyl, halogen, alkylhalos (e.g. $CF_3$), hydroxy, amino, alkoxy, alkylamino, acylamino, acyloxy, phenoxy, mercapto and both saturated and unsaturated cyclic hydrocarbons which are fused to the aromatic ring(s), linked covalently or linked to a common group such as a methylene or ethylene moiety. The linking group may also be a carbonyl such as in cyclohexyl phenyl ketone. The term "substituted aryl" encompasses "substituted arylalkyl."

"Substituted arylalkyl" defines a subset of "substituted aryl" wherein the substituted aryl group is attached to the nucleus shown in Formulae 1–4 by an alkyl group as defined herein.

The term "acyl" is used to describe a ketone substituent, —(O)R, where R is alkyl or substituted alkyl, aryl or substituted aryl as defined herein.

The term "halogen" is used herein to refer to fluorine, bromine, chlorine and iodine atoms.

The term "hydroxy" is used herein to refer to the group —CH.

The term "amino" is used to describe primary amines, R—$NH_2$.

The term "alkoxy" is used herein to refer to the —OR group, where R is a lower alkyl, substituted lower alkyl, aryl, substituted aryl, arylalkyl or substituted arylalkyl wherein the alkyl, aryl, substituted aryl, arylalkyl and substituted arylalkyl groups are as described herein. Suitable alkoxy radicals include, for example, methoxy, ethoxy, phenoxy, substituted phenoxy, benzyloxy, phenethyloxy, t-butoxy, etc.

The term "alkylamino" denotes secondary and tertiary amines wherein the alkyl groups may be either the same or different and are as described herein for "alkyl groups."

As used herein, the term "acylamino" describes substituents of the general formula RC(O)NR', wherein R' is a lower alkyl group and R represents the nucleus shown in Formulae 1–4 or an alkyl group, as defined herein, attached to the nucleus.

The term "acyloxy" is used herein to describe an organic radical derived from an organic acid by the removal of the acidic hydrogen. Simple acyloxy groups include, for example, acetoxy, and higher homologues derived from carboxylic acids such as ethanoic, propanoic, butanoic, etc. The acyloxy moiety may be oriented as either a forward or reverse ester (i.e. RC(O)OR' or R'OC(O)R, respectively, wherein R comprises the portion of the ester attached either directly or through an intermediate hydrocarbon chain to the nucleus shown in Formulae 1–4).

As used herein, the term "aryloxy" denotes aromatic groups which are linked to the nucleus shown in Formulae 1–4 directly through an oxygen atom. This term encompasses "substituted aryloxy" moieties in which the aromatic group is substituted as described above for "substituted aryl."

As used herein "aryloxyalkyl" defines aromatic groups attached, through an oxygen atom to an alkyl group, as defined herein. The alkyl group is attached to the nucleus shown in Formula 1–4. The term "aryloxyalkyl" encompasses "substituted aryloxyalkyl" moieties in which the aromatic group is substituted as described for "substituted aryl."

As used herein, the term "mercapto" defines moieties of the general structure R—S—R' wherein R and R' are the same or different and are alkyl, aryl or heterocyclic as described herein.

The term "saturated cyclic hydrocarbon" denotes groups such as the cyclopropyl, cyclobutyl, cyclopentyl, etc., and substituted analogues of these structures. These cyclic hydrocarbons can be single- or multi-ring structures.

The term "unsaturated cyclic hydrocarbon" is used to describe a monovalent non-aromatic group with at least one double bond, such as cyclopentene, cyclohexene, etc. and substituted analogues thereof. These cyclic hydrocarbons can be single- or multi-ring structures.

The term "heteroaryl" as used herein refers to aromatic rings in which one or more carbon atoms of the aromatic ring(s) are substituted by a heteroatom such as nitrogen, oxygen or sulfur. Heteroaryl refers to structures which may be a single aromatic ring, multiple aromatic ring(s), or one or more aromatic rings coupled to one or more non-aromatic ring(s). In structures having multiple rings, the rings can be fused together, linked covalently, or linked to a common group such as a methylene or ethylene moiety. The common linking group may also be a carbonyl as in phenyl pyridyl ketone. As used herein, rings such as thiophene, pyridine, isoxazole, phthalimide, pyrazole, indole, furan, etc. or benzo-fused analogues of these rings are defined by the term "heteroaryl."

"Heteroarylalkyl" defines a subset of "heteroaryl" wherein an alkyl group, as defined herein, links the heteroaryl group to the nucleus shown in Formulae 1–4.

"Substituted heteroaryl" refers to heteroaryl as just described wherein the heteroaryl nucleus is substituted with one or more functional groups such as lower alkyl, acyl, halogen, alkylhalos (e.g. $CF_3$), hydroxy, amino, alkoxy, alkylamino, acylamino, acyloxy, mercapto, etc. Thus, substituted analogues of heteroaromatic rings such as thiophene, pyridine, isoxazole, phthalimide, pyrazole, indole, furan, etc. or benzo-fused analogues of these rings are defined by the term "substituted heteroaryl."

"Substituted heteroarylalkyl" refers to a subset of "substituted heteroaryl" as described above in which an alkyl group, as defined herein, links the heteroaryl group to the nucleus shown in Formulae 1–4.

The term "heterocyclic" is used herein to describe a monovalent saturated or unsaturated non-aromatic group having a single ring or multiple condensed rings from 1–12 carbon atoms and from 1–4 heteroatoms selected from nitrogen, sulfur or oxygen within the ring. Such heterocycles are, for example, tetrahydrofuran, morpholine, piperidine, pyrrolidine, etc.

The term "substituted heterocyclic" as used herein describes a subset of "heterocyclic" wherein the heterocycle nucleus is substituted with one or more functional groups such as lower alkyl, acyl, halogen, alkylhalos (e.g. $CF_3$), hydroxy, amino, alkoxy, alkylamino, acylamino, acyloxy, mercapto, etc.

The term "heterocyclicalkyl" defines a subset of "heterocyclic" wherein an alkyl group, as defined herein, links the heterocyclic group to the nucleus shown in Formulae 1–4.

"Alkylsulfur," as used herein, encompasses, thiols, sulfides, disulfides and derivatives of these compounds wherein the alkyl group is substituted as described above for "substituted alkyl."

Metals can be plated onto particles, such as silica gel particles using electroless plating techniques to produce micrometer-sized particles with a metal layer substantially coating the particle surface. In a particularly preferred embodiment, the metal coating comprises a metal that forms a bond or intimate association (e.g., chemisorption, physisorption) with the an organic molecule, such as an organosulfur (e.g., alkylthiol, sulfide, disulfide). The metal coated particles can be surface-functionalized with SAMs (mixed and homogeneous) formed from organosulfur moieties.

Thus, in a first aspect, the invention provides a multilayered material comprising, a particulate substrate; a metal film layered onto the substrate; and an organic layer attached to the metal film.

In a preferred embodiment, the organic layer comprises a recognition moiety attached to a member selected from the group consisting of the organic layer, the metal film and combinations thereof. The recognition moiety is a molecule or portion of a molecule that interacts with a second molecule, referred to herein as the analyte.

In a further preferred embodiment, the recognition moiety is a member selected from the group consisting of biomolecules, organic groups, metal chelates and organometallic moieties. In another preferred embodiment, an organic group is a member selected from the group consisting of amines, carboxylic acids, drugs, chelating agents, crown ethers, cyclodextrins and combinations thereof. In a still further preferred embodiment, the biomolecule is a member selected from the group consisting of antibodies, antigens, carbohydrates, nucleic acids, peptides, enzymes and receptors.

In a second aspect, the invention provides a multilayered material comprising, a silica substrate; a metal film layered onto the substrate; an organic layer attached to the metal film; and a recognition moiety attached to a member selected from the group consisting of the organic layer, the metal film and combinations thereof.

In a third aspect, the present invention provides a multilayered material comprising, a silica substrate; a metal film layered onto the substrate; an organosulfur layer attached to the metal film; and a recognition moiety attached to the organosulfur layer.

In this aspect of the invention, the organic layer comprises at least one species, attached to the layer of gold, that has a recognition moiety as part of its molecular structure. In addition to the molecule bearing the recognition moiety, the organic layer can be mixed with other species that do not bear recognition moieties.

A. Particulate Substrates

Particulate substrates that are useful in practicing the present invention can be made of practically any physico-chemically stable material. Substrates can be selected from the group consisting of optically opaque substrates, optically transparent substrates, insulating substrates, conducting substrates, semiconducting substrates, magnetic substrates and combinations thereof.

Useful particulate substrates are not limited to a size or range of sizes. The choice of an appropriate particle size for a given application will be apparent to those of skill in the art. In certain preferred embodiments, the substrate has a diameter of from about 1 micrometer to about 1000 micrometers. In other preferred embodiments, the substrate has a diameter of from about 50 micrometers to about 500 micrometers.

Exemplary substrate materials include, but are not limited to, inorganic crystals, inorganic glasses, inorganic oxides, metals, organic polymers and combinations thereof.

A.1a. Inorganic Crystals and Glasses

Inorganic crystals and inorganic glasses that are appropriate for substrate materials include, for example, LiF, NaF, NaCl, KBr, KI, $CaF_2$, $MgF_2$, $HgF_2$, BN, $AsS_3$, ZnS, $Si_3N_4$ and the like. The crystals and glasses can be prepared by art standard techniques. See, for example, Goodman, CRYSTAL GROWTH THEORY AND TECHNIQUES, Plenum Press, New York, 1974. Alternatively, the crystals and glasses can be purchased commercially (e.g., Fischer Scientific, Duke Scientific Corporation, Palo Alto, Calif). The crystals and glasses can be the sole component of the substrate or they can be coated with one or more additional substrate components. Thus, it is within the scope of the present invention to utilize crystals and/or glasses coated with, for example one or more metal films or a metal film and an organic polymer. Additionally, a crystal and/or glass can constitute a portion of a substrate that contacts another portion of the substrate made of a different material, or a different physical form (e.g., a glass) of the same material. Other useful substrate configurations utilizing inorganic crystals and/or glasses will be apparent to those of skill in the art.

A.1b. Inorganic Oxides

Inorganic oxides can also form a substrate of the device of the present invention. Inorganic oxides of use in the present invention include, for example, $Cs_2O$, $Mg(OH)_2$, $TiO_2$, $ZrO_2$, $CeO_2$, $Y_2O_3$, $Cr_2O_3$, $Fe_2O_3$, NiO, ZnO, $Al_2O_3$, $SiO_2$ (glass), silica, quartz, $In_2O_3$, $SnO_2$, $PbO_2$ and the like. The inorganic oxides can be utilized in a variety of physical forms such as powders, glasses, crystals and the like. A substrate can consist of a single inorganic oxide or a composite of more than one inorganic oxide. For example, a composite of inorganic oxides can have a layered structure (i.e., a second oxide deposited on a first oxide) or two or more oxides can be arranged in a contiguous non-layered structure. In addition, one or more oxides can be admixed as particles of various sizes and deposited on a support such as a glass or metal sheet. Further, a layer of one or more inorganic oxides can be intercalated between two other substrate layers (e.g., metal-oxide-metal, metal-oxide-crystal). Appropriate inorganic oxide particles can be prepared or, alternatively, they can be purchased from commercial sources (e.g., Duke Scientific Corporation, Palo Alto, Calif.).

In a preferred embodiment, the substrate is a member selected from the group consisting of silicon oxides and aluminum oxides. In this embodiment, the substrate consists of a silica or alumina particle onto which a metal, such as gold is layered by electroless deposition.

A.1c. Metals

Metals are also of use as particulate substrates in the present invention. The metal can be used as a crystal or an amorphous material, such as a powder. Appropriate metal particles are available from a variety of sources (e.g., Duke Scientific Corporation, Palo Alto, Calif.). As most of the surface characteristics of the metal particle will be masked by its metallic coating layer, there are essentially no limitations on the types identity of metal that can be used in the present invention. The metal particles can be selected for desirable physical properties such as density, magnetic characteristics, heat capacity and the like.

A.1d. Organic Polymers

Organic polymers that form useful substrates include, for example, polyalkenes (e.g., polyethylene, polyisobutene, polybutadiene), polyacrylics (e.g., polyacrylate, polymethyl methacrylate, polycyanoacrylate), polyvinyls (e.g., polyvinyl alcohol, polyvinyl acetate, polyvinyl butyral, polyvinyl chloride), polystyrenes, polycarbonates, polyesters, polyurethanes, polyamides, polyimides, polysulfone, polysiloxanes, polyheterocycles, cellulose derivative (e.g., methyl cellulose, cellulose acetate, nitrocellulose), polysaccharides (e.g., dextran derivatives), polysilanes, fluorinated polymers, epoxies, polyethers and phenolic resins.

Many commercially available polymers and resins can also be used in practicing the present invention. These include, for example, Amberite™, Amberlyst™ and Dowex™ resins. Dextran derivatives such as Sephadex™ and analogous products. Polyamide resins, peptide synthesis resins and controlled pore glass. Moreover, commercially available particles of well-defined size and composition are available over a wide size range (Duke Scientific Corporation, Palo Alto, Calif.) and composed of a number of different materials, including polystyrene-latex, polystyrene-divinylbenzene.

Presently preferred organic polymers include carbohydrates, polycarbonates and polystyrene derivatives.

B. Metal Coatings

Metals that are presently preferred as coatings for particulate substrates include, but are not limited to, gold, silver, platinum, palladium, nickel and copper. Silver and gold are preferred, gold being particularly preferred.

The metal coating can be either continuous or discontinuous. Further, the thickness of the metal layer can remain constant or it can vary over the surface of the particulate substrate. In one embodiment, more than one metal is used. The more than one metal can be present as an alloy, they can be formed into a layered "sandwich" structure, or they can be laterally adjacent to one another. In a preferred embodiment, where more than one metal layer is used, the outermost metal is gold. In a particularly preferred embodiment the metal used is gold layered on silver, more preferably gold layered on silver which has been layered onto a particle activated by the adsorption of tin.

A wide range of art-recognized techniques leading to the deposition of a metal layer onto a substrate are appropriate for use in practicing the present invention. In a preferred embodiment, the metal is deposited by an electroless plating method.

Metals can be plated onto particles using electroless plating teclniques to produce micrometer-sized particles with a metal layer substantially coating the particle surface. In a particularly preferred embodiment, the metal coating comprises a metal that forms a bond or intimate association (e.g., chemisorption, physisorption) with an organic molecule, such as an organosulfur (e.g., alkylthiol, sulfide, disulfide). The metal coated particles can be surface-functionalized with SAMs (mixed and homogeneous) formed from organosulfur moieties.

In a presently preferred embodiment, the particle is a silica gel particle that is coated with gold by an electroless process. An organic layer is associated with the gold surface. Due to the extensive literature on their synthesis and characterization and the commercial availability of many species having useful structures and properties, ω-substituted alkyl-sulfur compounds are preferred as components of the organic layer.

C. Organic Layers

A wide variety of organic layers are useful in practicing the present invention. These organic layers can comprise monolayers, bilayers and multilayers. Furthermore, the organic layers can be attached by covalent bonds, ionic bonds, physisorption, chemisorption and the like, including, but not limited to, hydrophobic interactions, hydrophilic interactions, van der Waals interactions and the like.

In a presently preferred embodiment, organic layer components which form self-assembled monolayers are used.

In the discussion that follows, self-assembled monolayers are utilized as an exemplary organic layer. This use is not intended to be limiting. It will be understood that the various configurations of the self-assembled monolayers and their methods of synthesis, binding properties and other characteristics are equally applicable to each of the organic layers of use in the present invention.

C.1 Self-Assembled Monolayers ("SAMs")

Self-assembled monolayers are generally depicted as an assembly of organized, closely packed linear molecules. There are two widely-used methods to deposit molecular monolayers on solid substrates: Langmuir-Blodgett transfer and self-assembly. Additional methods include techniques such as depositing a vapor of the monolayer precursor onto a substrate surface. Each of these methods is appropriate for use in practicing the present invention.

The composition of a SAM useful in the present invention, can be varied over a wide range of compound structures and molar ratios. In one embodiment, the SAM is formed from only one compound. In a presently preferred embodiment, the SAM is formed from two or more compounds. In another preferred embodiment, the organic layer comprises a plurality of compounds, each compound comprising a moiety which associates with the metal film.

In yet a further preferred embodiment, the organic layer comprises a group having the structure:

$-SR^1(X^1)_n$ wherein $R^1$ is a linking group between sulfur and $X^1$; $X^1$ is a member selected from the group consisting of H, halogen, recognition moieties, hydrophilic polymers and combinations thereof; and n is a number between 1 and 50.

In a preferred embodiment, the SAM component bearing $X^1$ is attached directly and essentially irreversibly via a "stable bond" to the surface of the substrate. A "stable bond", as used herein, is a bond which maintains its chemical integrity over a wide range of conditions (e.g., amide, carbamate, carbon-carbon, ether, etc.). In another preferred embodiment the SAM component bearing the recognition moiety comprises a "cleaveable bond". A "cleaveable bond," as used herein, is a bond which undergoes scission under conditions which do not degrade other bonds in the recognition moiety-analyte complex. Cleaveable bonds include, but are not limited to, disulfide, imine, carbonate and ester bonds.

Exemplary applications wherein it is preferred that the molecule ("analyte") that interacts with $X^1$ remains tethered to the surface include, but are not limited to, quantitating or measuring a property of the analyte while it is tethered to the surface. Alternatively, the material of the invention can be used to remove an analyte from a liquid or vapor mixture to purify or partially purify that mixture or the analyte. Many other applications wherein the analyte remains tethered to the surface will be apparent to those of skill in the art.

Preferred $R^1$ groups with "stable" bonds include $R^1$ groups which are members selected from the group consisting of alkyl, substituted alkyl, aryl, arylalkyl, substituted aryl, substituted arylalkyl, saturated cyclic hydrocarbon, unsaturated cyclic hydrocarbon, heteroaryl, heteroarylalkyl, substituted heteroaryl, substituted heteroarylalkyl, heterocyclic, substituted heterocyclic and heterocyclicalkyl groups. Further preferred stable $R^1$ groups are members selected from the group consisting of alkyl and substituted alkyl groups.

Exemplary applications wherein the analyte or $X^1$-analyte complex be removable from the surface include, but are not limited to, purification of an analyte, synthesis of a molecule on the material of the invention and regeneration of the material of the invention.

Many cleaveable groups are known in the art. See, for example, Jung et al., *Biochem. Biophys. Acta*, 761: 152–162 (1983); Joshi et al., *J. Biol. Chem.*, 265: 14518–14525 (1990); Zarling et al., *J. Immunol.*, 124: 913–920 (1980); Bouizar et al., *Eur. J. Biochem.*, 155: 141–147 (1986); Park et al., *J. Biol. Chem.*, 261: 205–210 (1986); Browning et al., *J. Immunol.*, 143: 1859–1867 (1989). Exemplary cleaveable moieties can be cleaved using light, heat or reagents such as thiols, hydroxylamine, bases, periodate and the like. Preferred cleaveable groups comprise a cleaveable moiety which is a member selected from the group consisting of disulfide, ester, imide, carbonate, nitrobenzyl, phenacyl and benzoin groups.

When two or more structurally distinct moieties are used as components of the SAMs, the components can be contacted with the substrate as a mixture of SAM components or, alternatively, the components can be added sequentially. In those embodiments in which the SAM components are added as a mixture, the mole ratio of a mixture of the components in solution generally results in the same ratio in the mixed SAM. Depending on the manner in which the SAM is assembled, the two components do not phase segregate into islands. See, Bain et al., *J. Am. Chem. Soc.*, 111: 7164 (1989). This feature of SAMs can be used to immobilize recognition moieties or bulky modifying groups in such a manner that certain interactions, such as steric hindrance, between these molecules is minimized.

The individual components of the SAMs can also be bound to the substrate in a sequential manner. Thus, in one embodiment, a first SAM component is attached to the substrate's surface by "underlabeling" the surface functional groups with less than a stoichiometric equivalent of the first component. The first component can be a SAM component linked to a reactive group or recognition group, a spacer arm or a monovalent moiety. Subsequently, the second component is contacted with the substrate. This second component can either be added in stoichiometric equivalence, stoichiometric excess or can again be used to underlabel to leave sites open for yet a third component. It is also possible to displace some fraction of the first adsorbed species by a second species, thereby forming a mixture on the surface.

In certain preferred embodiments, the organic layer comprises:

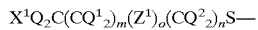

wherein, $X^1$ is a member selected from the group consisting of H, halogen and recognition moieties; Q, $Q^1$ and $Q^2$ are independently members selected from the group consisting of H and halogen; $Z^1$ is a member selected from the group consisting of —$CQ_2$—, —$CQ^1{}_2$—, —$CQ^2{}_2$—, —O—, —S—, —$NR^1$—, —$C(O)NR^1$ and $R^1NC(O)$—, in which; $R^1$ is a member selected from the group consisting of H, alkyl, substituted alkyl, aryl, substituted aryl, heteroaryl and heterocyclic groups; m is a number between 0 and 40; and n is a number between 0 and 40 and o is a number between 0 and 5.

In yet a further preferred embodiment, the Q, $Q^1$ and $Q^2$ are independently members selected from the group consisting of H and fluorine. In a further preferred embodiment, $R^2$ is a member selected from H and $CH_3$. In yet another preferred embodiment u is a number between 5 and 20.

When the organic layer is formed from a halogenated organosulfur compound, the organic layer can comprise a single halogenated compound or more than one halogenated compound having different structures. Additionally, these layers can comprise both non-halogenated and halogenated organosulfur compounds.

In certain preferred embodiment of this aspect of the invention, the organosulfur layer comprises a member selected from the group consisting of —$S(CH_2)_n OH$, —$S(CH_2)_n COOH$, —$S(CH_2)_n CH_3$, $HOCH_2CH_2(OCH_2CH_2)_m S$— and combinations thereof; m is an integer between 2 and 50; and n is an integer between 1 and 25. In a still further preferred embodiment, n is an integer between 5 and 15. In certain embodiment, the organic layer will include only these molecules, while in others one or more of these species will be mixed with one or more additional species.

Although, each of the components of the organic layer discussed herein are appropriate for practicing this aspect of the invention, in preferred embodiments, the organosulfur layer further comprises —$S(CH_2)_m X^1$, wherein $X^1$ is a recognition moiety; and m is an integer from 1 to 25. In another preferred embodiment, m is an integer from to 15.

C.2 Hydrophilic Polymers

In a preferred embodiment, the organic layer includes a hydrophilic polymer. The hydrophilic polymer can comprise an $X^1$ or not. A number of hydrophilic polymers are useful in practicing the present invention. Both charged and uncharged polymers are of use, however, uncharged polymers are preferred. Suitable uncharged polymers include, but are not limited to, polyethylene glycol (PEG), poly (vinylalcohol), poly(propyleneglycol) (PPG)-PEG co-polymers PEG-PPG co-block polymers and similar polymers. In a preferred embodiment, these polymers are derivatized with at least one sulfur-containing moiety. PEG-thiols of various molecular weights are commercially available (Shearwater Polymers, Huntsville, Ala.). The choice of an appropriate polymer and its modification for a particular purpose will be apparent and readily accessible to those of skill in the art.

In a further preferred embodiment, $R^1$ is a poly (ethyleneglycol) moiety. Polyethylene glycol (PEG) use in biotechnology and biomedical applications continues to expand and has been reviewed (POLY(ETHYLENE GLYCOL) CHEMISTRY. BIOTECHNICAL AND BIOMEDICAL APPLICATIONS, J. M. Harris, Ed., Plenum Press, New York, 1992). Modification of enzymes (Chiu el al., *J. Bioconjugate Chem.*, 4: 290–295 (1993)), RGD peptides (Braatz et al., *Bioconjugate Chem.*, 4: 262–267 (1993)), liposomes (Zalipsky, S. *Bioconjugate Chem.*, 4: 296–299 (1993)), and CD4-IgG glycoprotein (Chamow et al., *Bioconjugate Chem.*, 4: 133–140 (1993)) are some of the recent advances in the use of polyethylene glycol. The modification of toxicity, pharmacokinetics, biodistribution and other biofunctions are a number of the promising areas for the use of this simple polymer. Surfaces treated with PEG have been shown to resist protein deposition and have improved resistance to thrombogenicity when coated on blood contacting biomaterials (Merrill, "Poly(ethylene oxide) and Blood Contact: A Chronicle of One Laboratory," in POLY(ETHYLENE GLYCOL) CHEMISTRY: BIO-TECHNICAL AND BIOMEDICAL APPLICATIONS, Harris, Ed., Plenum Press, New York, (1992), pp. 199–220). Accordingly, application of PEG based coatings to multi-layered particulate materials would be very useful for chromatography, analytical and medical devices.

Poly(ethyleneglycol) is known to impart hydrophilicity and protein adsorption resistance and to reduce the immunogenicity and antigenicity of materials to which it is bound. See, for example, Abuchowski et al., ENZYMES AS DRUGS, Holcenberg et al, Eds., John Wiley & Sons, N.Y., (1981), pp. 367–383. Many methods are available in the art for attaching poly(ethyleneglycol) moieties to other molecules. Generally, to effect covalent attachment of polyethylene glycol (PEG) to another molecule, for example, a protein, the hydroxyl end-groups of the polymer are first converted into reactive functional groups. This process is frequently referred to as "activation" and the product is called "activated PEG".

Many activated derivatives of poly(cthyleneglycol) are available commercially and in the literature. It is well within the abilities of one of skill to choose, and synthesize if necessary, an appropriate activated PEG derivative. At present, the most common form of activated PEG used for preparation of protein conjugates is poly(ethylene glycol) succinoyl-N-hydroxysuccinimide ester (SS-PEG). This derivative reacts quickly with proteins (30 min) under mild conditions yielding active yet extensively modified conjugates and, thus, is appropriate for use in practicing the present invention. See, Abuchowski et al. *Cancer Biochem. Biophys.,* 7: 175–186 (1984). In addition, many other activated PEG groups can be used in the present invention. Some of these are detailed below.

Activation of PEG has been reported to be accomplished by the use of reactive functional groups including cyanurylate (Abuchowski et al., *J. Biol. Chem.,* 252: 3582–3586 (1977); Jackson et al., *Anal. Biochem.,* 165: 114–127 (1987); Koide et al., *Biochem Biophys. Res. Commun.,* 111: 659–667 (1983)), tresylate (Nilsson et al., *Methods Enzymol.,* 104: 56–69 (1984); Delgado et al., *Biotechnol. Appl. Biochem.,* 12: 119–128 (1990)); N-hydroxysuccinimide derived active esters (Buckmann et al., *Makromol. Chem.,* 182: 1379–1384 (1981); Joppich et al., *Makromol. Chem.,* 180: 1381–1384 (1979); Abuchowski et al., *Cancer Biochem. Biophys.,* 7: 175–186 (1984); Katreet al. *Proc. Natl. Acad. Sci. U.S.A.,* 84: 1487–1491 (1987); Kitamura et al., *Cancer Res.,* 51: 4310–4315 (1991); Boccu et al., *Z. Naturforsch.,* 38C: 94–99 (1983), carbonates (Zalipsky et al., POLY (ETHYLENE GLYCOL) CHEMISTRY: BIOTECHNICAL AND BIOMEDICAL APPLICATIONS, Harris, Ed., Plenum Press, New York, 1992, pp. 347–370; Zalipsky el al, *Biotechnol. Appl. Biochem.,* 15: 100–114 (1992); Veronese et al., *Appl. Biochem. Biotech.,* 11: 141–152 (1985)), imidazolyl formates (Beauchamp et aL, *Anal. Biochem.,* 131: 25–33 (1983); Berger et al., *Blood,* 71: 1641–1647 (1988)), 4-dithiopyridines (Woghiren et al., *Bioconjugate Chem.,* 4: 314–318 (1993)), isocyanates (Byun et al., *ASAIO Journal,* M649-M-653 (1992)) and epoxides (U.S. Pat. No. 4,806, 595, issued to Noishiki et al., (1989). Other linking groups include the urethane linkage between amino groups and activated PEG. See, Veronese, et al., *Appl. Biochem. Biotechnol.,* 11: 141–152 (1985).

Various activated polyethylene glycols (PEG) have been effectively used in such fields as protein modification (Abuchowski & Davis, 1981, supra), peptide chemistry (Zalipsky, el al., *Int, J. Peptide Protein Res.,* 30: 740–783 (1987)) and preparation of conjugates with biologically active materials (Zalipsky, et aL, *Eur. Polym. J.,* 19: 1177–1183 (1983) and Zalipsky et al., *Polymer Preprints, Am. Chem. Soc. Div. Polym. Chem.,* 27(1): 1–2 (1986)).

Also of use in the present invention are succinidyl carbonate activated PEGs, namely, poly(ethylene glycol)-succinidyl carbonate (SC-PEG). These materials react to yield attachment through stable urethane linkages. The reactivity of these agents, are comparable to the conventionally used SS-PEG. Thus, high degrees of modification are achievable in mild conditions (aqueous buffers, pH 5.8–11, preferably pH 7.0–9.5) within about 30–60 min. and moderate temperatures (4°–40° C.). Additionally, the agents are soluble in a variety of organic solvents, thus being useful and important in the coupling of low molecular weight, partially protected peptides and other biologically useful ligands. See, U.S. Pat. No. 5,122,614, issued Jun. 16, 1992 to Zalipsky.

PEG useful in practicing the present invention does not have to be of a particular molecular weight, but it is preferred that the molecular weight be between 500 and 40,000; more preferably between 2,000 and 20,000.

In other preferred embodiments, the PEG does not have an $X^1$ group at a terminus and the organic layer comprises:

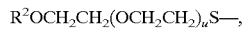

$$R^2OCH_2CH_2(OCH_2CH_2)_uS\text{---},$$

in which $R^2$ is a member selected from the group consisting of H, alkyl and acyl; and u is a number between 1 and 50.

D. RECOGNITION MOIETIES

As used herein, the term "recognition moiety" refers to molecules which are attached to one or more organic layer components. The recognition moieties can interact with the analyte via either attractive or repulsive mechanisms. In one exemplary embodiment, the analyte and the recognition moiety form an intimately associated pair by, for example, covalent bonding, ionic bonding, ion pairing, van der Waals association and the like. In another exemplary embodiment, the analyte and recognition moiety interact by a repulsive mechanism such as incompatible steric characteristics, charge-charge repulsion, hydrophilic-hydrophobic interactions and the like.

Recognition moieties can be selected from a wide range of small organic molecules (e.g., drugs, pesticides, toxins, etc.), organic functional groups (e.g., amines, carbonyls, carboxylates, etc.), biomolecules, metals, metal chelates and organometallic compounds.

When the recognition moiety is an amine, in preferred embodiments, the recognition moiety will interact with a structure on the analyte which reacts by interacting (e.g., binding, complexing) with the amine (e.g., carbonyl groups, alkylhalo groups). In another preferred embodiment, the amine is protonated by an acidic moiety on the analyte of interest (e.g., carboxylic acid, sulfonic acid).

In certain preferred embodiments, when the recognition moiety is a carboxylic acid, the recognition moiety will interact with the analyte by, for example, complexation (e.g., metal ions). In still other preferred embodiments, the carboxylic acid will protonate a basic group on the analyte (e.g. amine).

In another preferred embodiment, the recognition moiety is a drug moiety. The drug moieties can be agents already accepted for clinical use or they can be drugs whose use is experimental, or whose activity or mechanism of action is under investigation. The drug moieties can have a proven action in a given disease state or can be only hypothesized to show desirable action in a given disease state. In a preferred embodiment, the drug moieties are compounds which are being screened for their ability to interact with an analyte of choice. As such, drug moieties which are useful in practicing the instant invention include drugs from a broad range of drug classes having a variety of pharmacological activities.

Classes of useful agents include, for example, non-steroidal anti-inflammatory drugs (NSAIDS). The NSAIDS can, for example, be selected from the following categories: (e.g., propionic acid derivatives, acetic acid derivatives, fenamic acid derivatives, biphenylcarboxylic acid derivatives and oxicams); steroidal anti-inflammatory drugs including hydrocortisone and the like; antihistaminic drugs (e.g., chlorpheniramine, triprolidine); antitussive drugs (e.g., dextromethorphan, codeine, carmiphen and carbetapentane); antipruritic drugs (e.g., methidilizine and trimeprizine); anticholinergic drugs (e.g., scopolamine, atropine, homatropine, levodopa); anti-emetic and antinauseant drugs (e.g., cyclizine, meclizine, chlorpromazine, buclizine); anorexic drugs (e.g., benzphetamine, phentermine, chlorphentermine, fenfluramine); central stimulant drugs (e.g., amphetamine, methamphetamine, dextroamphetamine and methylphenidate); antiarrhythmic drugs (e.g., propanolol, procainamide, disopyraminde, quinidine, encainide); β-adrenergic blocker drugs (e.g., metoprolol, acebutolol, betaxolol, labetalol and timolol); cardiotonic drugs (e.g., milrinone, amrinone and dobutamine); antihypertensive drugs (e.g., enalapril, clonidine, hydralazine, minoxidil, guanadrel, guanethidine) ;diuretic drugs (e.g., amiloride and hydrochlorothiazide); vasodilator drugs (e.g., diltazem, amiodarone, isosuprine, nylidrin, tolazoline and verapamil); vasoconstrictor drugs (e.g., dihydroergotamine, crgotamine and methylsergide); antiulcer drugs (e.g., ranitidine and cimetidine); anesthetic drugs (e.g., lidocaine, bupivacaine, chlorprocaine, dibucaine); antidepressant drugs (e.g., imipramine, desipramine, amitryptiline, nortryptiline); tranquilizer and sedative drugs (e.g., chlordiazepoxide, benacytyzine, benzquinamide, flurazapam, hydroxyzine, loxapine and promazine); antipsychotic drugs (e.g., chlorprothixene, fluphenazine, haloperidol, molindone, thioridazine and trifluoperazine); antimicrobial drugs (antibacterial, antifungal, antiprotozoal and antiviral drugs).

Antimicrobial drugs which are preferred for incorporation into the present composition include, for example, pharmaceutically acceptable salts of β-lactam drugs, quinolone drugs, ciprofloxacin, norfloxacin, tetracycline, erythromycin, amikacin, triclosan, doxycycline, capreomycin, chlorhexidine, chlortetracycline, oxytetracycline, clindamycin, ethambutol, hexamidine isothionate, metronidazole, pentamidine, gentamycin, kanamycin, lineomycin, methacycline, methenamine, minocycline, neomycin, netilmycin, paromomycin, streptomycin, tobramycin, miconazole and amanfadine.

Other drug moieties of use in practicing the present invention include antineoplastic drugs (e.g., antiandrogens (e.g., leuprolide or flutamide), cytocidal agents (e.g., adriamycin, doxorubicin, taxol, cyclophosphamide, busulfan, cisplatin, α-2-interferon) anti-estrogens (e.g., tamoxifen), antimetabolites (e.g., fluorouracil, methotrexate, mercaptopurine, thioguanine).

The recognition moiety can also comprise hormones (e.g., medroxyprogesterone, estradiol, leuprolide, megestrol, octreotide or somatostatin);

muscle relaxant drugs (e.g., cinnamedrine, cyclobenzaprine, flavoxate, orphenadrine, papaverine, mebeverine, idaverine, ritodrine, dephenoxylate, dantrolene and azumolen); antispasmodic drugs; bone-active drugs (e.g., diphosphonate and phosphonoalkylphosphinate drug compounds); endocrine modulating drugs (e.g., contraceptives (e.g., ethinodiol, ethinyl estradiol, norethindrone, mestranol, desogestrel, medroxyprogesterone), modulators of diabetes (e.g., glyburide or chlorpropamide), anabolics, such as testolactone or stanozolol, androgens (e.g., methyltestosterone, testosterone or fluoxymesterone), antidiuretics (e.g., desmopressin) and calcitonins).

Also of use in the present invention are estrogens (e.g., diethylstilbesterol), glucocorticoids (e.g., triamcinolone, betamethasone, etc.) and progenstogens, such as norethindrone, ethynodiol, norethindrone, levonorgestrel; thyroid agents (e.g., liothyronine or levothyroxine) or anti-thyroid agents (e.g., methimazole); antihyperprolactinemic drugs (e.g., cabergoline); hormone suppressors (e.g., danazol or goserelin), oxytocics (e.g., methylergonovine or oxytocin) and prostaglandins, such as mioprostol, alprostadil or dinoprostone, can also be employed.

Other useful recognition moieties include immunomodulating drugs (e.g., antihistamines, mast cell stabilizers, such as lodoxamide and/or cromolyn, steroids (e.g., triamcinolone, beclomethazone, cortisone, dexamethasone, prednisolone, methylprednisolone, beclomethasone, or clobetasol), histamine $H_2$ antagonists (e.g., famotidine, cimetidine, ranitidine), immunosuppressants (e.g., azathioprine, cyclosporin), etc. Groups with anti-inflammatory activity, such as sulindac, etodolac, ketoprofen and ketorolac, are also of use. Other drugs of use in conjunction with the present invention will be apparent to those of skill in the art.

The above enumerated, and other molecules, can be attached to the organic layer by methods well-known to those of skill in the art. Ample guidance can be found in literature devoted to, for example, the fields of bioconjugate chemistry and drug delivery. For example, one of skill, faced with a drug comprising an available amine will be able to choose from among a variety of amine derivatizing reactions, locate an appropriately functionalized partner (e.g., a carboxylic acid terminated thiol) for the organic layer and react the partners under conditions chosen to effect the desired coupling (e.g., dehydrating agents, e.g., dicyclohexylcarbodiimide). See, for example, MODIFICATION OF PROTEINS: FOOD, NUTRITIONAL, AND PHARMACOLOGICAL ASPECTS, Feeney et al., Eds., American Chemical Society, Washington, D.C., 1982, pp. 370–387; POLYMERIC DRUGS AND DRUG DELIVERY SYSTEMS, Dunn et al., Eds., American Chemical Society, Washington, D.C., 1991.

When the recognition moiety is a chelating agent, crown ether or cyclodextrin, host-guest chemistry will dominate the interaction between the recognition moiety and the analyte. The use of host-guest chemistry allows a great degree of recognition-moiety-analyte specificity to be engineered into a device of the invention. The use of these compounds to bind to specific compounds is well known to those of skill in the art. See, for example, Pitt et al., "The Design of Chelating Agents for the Treatment of Iron Overload," In, INORGANIC CHEMISTRY IN BIOLOGY AND MEDICINE; Martell, Ed.; American Chemical Society, Washington, D.C., 1980, pp. 279–312; Lindoy, THE CHEMISTRY OF MACROCYCLIC LIGAND COMPLEXES; Cambridge University Press, Cambridge,1989; Dugas, BIOORGANIC CHEMISTRY; Springer-Verlag, New York, 1989, and references contained therein.

Additionally, a manifold of routes allowing the attachment of chelating agents, crown ethers and cyclodextrins to other molecules is available to those of skill in the art. See, for example, Meares el al., "Properties of In Vivo Chelate-Tagged Proteins and Polypeptides." In, MODIFICATION OF PROTEINS: FOOD, NUTRITIONAL, AND PHARMACOLOGICAL ASPECTS;" Feeney, et al., Eds., American Chemical Society, Washington, D.C., 1982, pp. 370–387; Kasina et al., Bioconjugate Chem., 9: 108–117 (1998); Song et al., Bioconjugate Chem., 8: 249–255 (1997).

In another preferred embodiment, the recognition moiety forms an inclusion complex with the analyte of interest. In a particularly preferred embodiment, the recognition moiety is a cyclodextrin or modified cyclodextrin. Cyclodextrins are a group of cyclic oligosaccharides produced by numerous microorganisms. Cyclodextrins have a ring structure which has a basket-like shape. This shape allows cyclodextrins to include many kinds of molecules into their internal cavity. See, for example, Szejtli, CYCLODEXTRINS AND THEIR INCLUSION COMPLEXES; Akademiai Klado, Budapest, 1982; and Bender et al., CYCLODEXTRIN CHEMISTRY, Springer-Verlag, Berlin, 1978.

Cyclodextrins are able to form inclusion complexes with an array of organic molecules including, for example, drugs, pesticides, herbicides and agents of war. See, Tenjarla et al., J. Pharm. Sci., 87: 425–429 (1998); Zughul et al., Pharm. Dev. Technol., 3: 43–53 (1998); and Albers et al., Crit. Rev. Ther. Drug Carrier Syst., 12: 311–337 (1995). Importantly, cyclodextrins are able to discriminate between enantiomers of compounds in their inclusion complexes. Thus, in one preferred embodiment, the invention provides for the detection of a particular enantiomer in a mixture of enantiomers. See, Koppenhoefer et al., J. Chromatogr., A 793: 153–164 (1998).

The cyclodextrin recognition moiety can be attached to a SAM component, through a spacer arm or directly to the metal. See, Yamamoto et al., J. Phys. Chem. B, 101: 6855–6860 (1997). Methods to attach cyclodextrins to other molecules are well known to those of skill in the chromatographic and pharmaceutical arts. See, Sreenivasan, K. J., Appl. Polym. Sci., 60: 2245–2249 (1996).

In a presently preferred embodiment, the recognition moiety is a polyaminocarboxylate chelating agent such as ethylenediaminctetraacetic acid (EDTA) or diethylenetriaminepentaacetic acid (DTPA). These recognition moieties can be attached to any amine-terminated component of a SAM or a spacer arm, for example, by utilizing the commercially available dianhydride (Aldrich Chemical Co., Milwaukee, Wis.).

In still further preferred embodiments, the recognition moiety is a biomolecule such as a protein, nucleic acid, peptide or an antibody. Biomolecules useful in practicing the present invention can be derived from any source. The biomolecules can be isolated from natural sources or can be produced by synthetic methods. Proteins can be natural proteins or mutated proteins. Mutations can be effected by chemical mutagenesis, site-directed mutagenesis or other means of inducing mutations known to those of skill in the art. Proteins useful in practicing the instant invention include, for example, enzymes, antigens, antibodies and receptors. Antibodies can be either polyclonal or monoclonal. Peptides and nucleic acids can be isolated from natural sources or can be wholly or partially synthetic in origin.

In those embodiments wherein the recognition moiety is a protein or antibody, the protein can be tethered to a SAM component or a spacer arm by any reactive peptide residue available on the surface of the protein. In preferred embodiments, the reactive groups are amines or carboxylates. In particularly preferred embodiments, the reactive groups are the $\epsilon$-amine groups of lysine residues. Furthermore, these molecules can be adsorbed onto the surface of the substrate or SAM by non-specific interactions (e.g., chemisorption, physisorption).

Recognition moieties which are antibodies can be used to recognize analytes which are proteins, peptides, nucleic acids, saccharides or small molecules such as drugs, herbicides, pesticides, industrial chemicals and agents of war. Methods of raising antibodies for specific molecules are well-known to those of skill in the art. See, U.S. Pat. No. 5,147,786, issued to Feng et al. on Sep. 15, 1992; U.S. Pat. No. 5,334,528, issued to Stanker et al. on Aug. 2, 1994; U.S. Pat. No. 5,686,237, issued to Al-Bayati, M.A.S. on Nov. 11, 1997; and U.S. Pat. No. 5,573,922, issued to llocss et al. on Nov. 12, 1996. Methods for attaching antibodies to surfaces are also known in the art. See, Delamarche et al. Langmuir, 12: 1944–1946 (1996).

D.1 Reactive Groups

"Reactive groups," as used herein refers to a subset of recognition moieties. The members of this subset can be used to attach recognition moieties to SAM components or, alternatively, they can themselves serve as recognition moieties. For example, an amine-bearing SAM component can be used to bind a carboxylic acid-containing recognition moiety onto the SAM, or it can be used to "recognize" a carboxylic, or other acid, in a solution, vapor and the like. One principle of recognition using reactive groups can be broadly stated: materials having electron deficient (e.g., electrophilic) organic layers can be used to recognize electron rich (e.g., nucleophilic) species and vice-versa. Moreover, acids can be used to recognize bases and vice versa.

The reactive groups can also be used to tether recognition groups onto the materials of the invention either before or after the organic layer has been deposited onto the metal layer. In certain circumstances, it will be desirable to assemble a batch of the particulate material having a reactive group on its surface. The material can be stored and aliquots can be used to bind recognition moieties as the materials are needed. Alternatively, aliquots of the material can each be reacted with a different recognition moiety to, for example, screen or assemble a library of compounds. Many other variations of and uses for this strategy will be readily apparent to those of skill in the art. The nature of useful reactive groups is discussed in greater detail below.

The reactive functional groups can be chosen such that they do not participate in, or interfere with, the reaction controlling the attachment of the functionalized SAM component onto the substrate's surface. Alternatively, the reactive functional group can be protected from participating in the reaction by the presence of a protecting group. Those of skill in the art will understand how to protect a particular functional group from interfering with a chosen set of reaction conditions. For examples of useful protecting groups, see Greene et al., PROTECTIVE GROUPS IN ORGANIC SYNTHESIS, John Wiley & Sons, New York, 1991.

The discussion which follows focuses on the attachment of a reactive SAM component to the substrate surface. This focus is for convenience only and one of skill in the art will understand that the discussion is equally applicable to embodiments in which the SAM component-recognition moiety is preformed prior to its attachment to the substrate. As used herein, "reactive SAM components" refers to components that have a functional group available for reaction with a recognition moiety or other species following the attachment of the component to the substrate.

Currently favored classes of reactions available with reactive SAM components are those which proceed under relatively mild conditions. These include, but are not limited to nucleophilic substitutions (e.g., reactions of amines and alcohols with acyl halides), electrophilic substitutions (e.g., enamine reactions) and additions to carbon-carbon and carbon-heteroatom multiple bonds (e.g., Michael reaction, Diels-Alder addition). These and other useful reactions are discussed in March, ADVANCED ORGANIC CHEMISTRY, Third Ed., John Wiley & Sons, New York, 1985.

According to the present invention, a particle's surface can be functionalized with SAM components and other species by attaching a reactive SAM component to the substrate surface in such a way as to derivative the substrate surface with a plurality of available reactive functional groups. Reactive groups which can be used in practicing the present invention include, for example, amines, hydroxyl groups, carboxylic acids, carboxylic acid derivatives, alkenes, sulfhydryls, etc.

In a preferred embodiment, the reactive group is tethered to the metal surface by an agent displaying avidity for that surface. In a presently preferred embodiment, the substrate includes a silver film or a gold film and the group which reacts with the metal surface comprises a thiol, sulfide or disulfide such as:

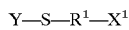

wherein $R^1$ is a linking group between sulfur and $X^1$ and $X^1$ is a reactive group or a protected reactive group. $X^1$ can also be a recognition moiety as discussed below. Y is a member selected from the group consisting of H, $R^2$ and $R^2$—S—, wherein $R^1$ and $R^2$ are independently selected. When $R^1$ and $R^2$ are the same, symmetrical sulfides and disulfides result, and when they are different, asymmetrical sulfides and disulfides result.

A large number of functionalized thiols, sulfides and disulfides are commercially available (Aldrich Chemical Co., St. Louis). Additionally, those of skill in the art have available to them a manifold of synthetic routes with which to produce additional such molecules. For example, amine-functionalized thiols can be produced from the corresponding halo-amines, halo-carboxylic acids, etc. by reaction of these halo precursors with sodium sulfhydride. See, for example, Reid, ORGANIC CHEMISTRY OF BIVALENT SULFUR, vol. 1, pp. 21–29, 32–35, vol. 5, pp. 27–34, Chemical Publishing Co., New York, 1958, 1963. Additionally, functionalized sulfides can be prepared via alkylthio-de-halogenation with a mercaptan salt. See, Reid, ORGANIC CHEMISTRY OF BIVALENT SULFUR, vol. 2, pp. 16–21, 24–29, vol. 3, pp. 11–14, Chemical Publishing Co., New York, 1960. Other methods for producing compounds useful in practicing the present invention will be apparent to those of skill in the art.

Many reactive groups and protected reactive groups of use in the present invention will be apparent to those of skill in the art. One of skill will be able to ascertain and purchase or synthesize the reactive organic layer constituent needed for a particular purpose. Representative reactive functional groups ($X^1$) include, but are not limited to:

(a) carboxyl groups and various derivatives thereof including, but not limited to, N-hydroxysuccinimide esters, N-hydroxybenztriazole esters, acid halides, acyl imidazoles, thioesters, p-nitrophenyl esters, alkyl, alkenyl, alkynyl and aromatic esters;

(b) hydroxyl groups which can be converted to esters, ethers, aldehydes, etc.

(c) haloalkyl groups wherein the halide can be later displaced with a nucleophilic group such as, for example, an amine, a carboxylate anion, thiol anion, carbanion, or an alkoxide ion, thereby resulting in the covalent attachment of a new group at the site of the halogen atom;

(d) dienophile groups which are capable of participating in Diels-Alder reactions such as, for example, maleimido groups;

(e) aldehyde or ketone groups such that subsequent derivatization is possible via formation of carbonyl derivatives such as, for example, imines, hydrazones, semicarbazones or oximes, or via such mechanisms as Grignard addition or alkyllithium addition;

(f) sulfonyl halide groups for subsequent reaction with amines, for example, to form sulfonamides;

(g) thiol groups which can be converted to disulfides or reacted with acyl halides;

(h) amine or sulfhydryl groups which can be, for example, acylated or alkylated;

(i) alkenes which can undergo, for example, cycloadditions, acylation, Michael addition, etc.; and (i) epoxides which can react with, for example, amines and hydroxyl compounds.

E. Conjugation

A recognition moiety can be conjugated to the surface of a SAM by any of a large number of art-known attachment methods. In one preferred embodiment, a reactive SAM component is attached to the substrate and the recognition moiety is subsequently bound to the SAM component via the reactive group on the SAM component and a group of complementary reactivity on the recognition moiety. See, for example, Hegner et al., *biophys J.*, 70: 2052–2066 (1996). In another preferred embodiment, the recognition moiety is attached to the SAM component prior to immobilizing the SAM component on the substrate surface: the recognition moiety-SAM component cassette is then attached to the substrate. In a still further preferred embodiment, the recognition moiety is attached to the substrate via a displacement reaction. In this embodiment, the SAM is preformed and then a fraction of the SAM components are displaced by a recognition moiety or a SAM component bearing a recognition moiety.

Peptides and nucleic acids can be attached to a SAM component. Both naturally-derived and synthetic peptides and nucleic acids are of use in conjunction with the present invention. These molecules can be attached to a SAM component by any available reactive group. For example, peptides can be attached through an amine, carboxyl, sulfhydryl, or hydroxyl group. Such a group can reside at a peptide terminus or at a site internal to the peptide chain. Nucleic acids can be attached through a reactive group on a base (e.g., exocyclic amine) or an available hydroxyl group on a sugar moiety (e.g., 3'- or 5'-hydroxyl). The peptide and nucleic acid chains can be further derivatized at one or more sites to allow for the attachment of appropriate reactive groups onto the chain. See, Chrisey et al., *Nucleic Acids Res.*, 24: 3031–3039 (1996).

When the peptide or nucleic acid is a fully or partially synthetic molecule, a reactive group or masked reactive group can be incorporated during the process of the synthesis. Many derivatized monomers appropriate for reactive group incorporation in both peptides and nucleic acids are know to those of skill in the art. See, for example, "Special Methods in Peptide Synthesis," In, THE PEPTIDES: ANALYSIS, SYNTHESIS, BIOLOGY, Vol.2: Gross, et aL., Eds., Academic Press, New York (1980). Many useful monomers are commercially available (Bachem, Sigma, etc.). This masked group can then be unmasked following the synthesis, at which time it becomes available for reaction with a SAM component or a spacer arm.

In other preferred embodiments, the peptide is attached directly to the metal film. See, Frey et al. *Anal. Chem.*, 68: 3187–3193 (1996). In a particularly preferred embodiment, the peptide is attached to a silver or a gold film through a sulfhydryl group on a cysteine residue. In another preferred embodiment, the peptide is attached through a thiol to a spacer arm which terminates in, for example, an iodoacetamide, chloroacetamide, benzyl iodide, benzyl bromide, alkyl iodide or alkyl bromide. Similar immobilization techniques are known to those of skill in the art. See, for example, Zull Iet al, *J. Ind. Microhiol.*, 13: 137–143 (1994).

F. Spacer Arms

As used herein, the term "spacer arm," refers to constituents of the organic layer that have a different structure than the bulk of the organic layer and which bear either reactive groups, recognition moieties or combinations thereof.

In certain embodiments, it is advantageous to have the recognition moiety attached to a SAM component having a structure that is different than that of the constituents of the bulk SAM. In this embodiment, the group to which the recognition moiety is bound is referred to as a "spacer arm" or "spacer." Using such spacer arms, the properties of the SAM adjacent to the reactive group and/or recognition moiety can be controlled. Properties that are usefully controlled include, for example, hydrophobicity, hydrophilicity, surface-activity and the distance of the reactive group and/or recognition moiety from the surface of the substrate and/or the SAM. For example, in a SAM composed of alkanethiols, the recognition moiety can be attached to the metal film or a SAM component via an amine terminated poly (ethyleneglycol). Numerous other combinations of spacer arms and SAMs will be apparent, and are accessible, to those of skill in the art.

In addition to the use of hydrophilic polymers, the hydrophilicity of the organic layer can be enhanced by reaction with polar molecules such as amine-, hydroxyl- and polyhydroxyl-containing molecules. Similar strategies can be used to increase hydrophobicity (e.g, use of long-chain fatty acid derivatives) and to enhance the surface activity of the material (e.g., use of detergents, surfactants).

In another embodiment, the spacer serves to distance the reactive group and/or recognition moiety from the substrate or SAM. Spacers with this characteristic have several uses. For example, a recognition moiety held too closely to the substrate or SAM surface may not react with incoming analyte, or it may react unacceptably slowly. When an analyte is itself sterically demanding, the reaction leading to recognition moiety-analyte complex formation can be undesirably slowed, or not occur at all, due to the monolithic substrate hindering the approach of the two components.

G. Methods

In addition to the novel materials detailed above, the present invention also includes methods for using and manufacturing these materials.

G.1 Molecular Capture

In a fourth aspect, the present invention provides a method of capturing a molecule comprising:
  contacting the molecule with the multilayered material comprising;
    a particulate substrate;
    a metal film layered onto the substrate;
    an organic layer attached to the metal film; and
    a recognition moiety attached to a member selected from the group consisting of the organic layer, the metal film and combinations thereof, wherein the recognition moiety associates with the molecule forming a multilayered material-molecule complex, thereby capturing the molecule.

As used herein, the term "capture" refers to an interaction between a group on the particulate material of the invention and a complementary group on an analyte. The interaction can be either reversible or irreversible. Molecules can be captured from a variety of milieus, including pure liquids, solutions, gases, vapors and the like.

This aspect of the invention can be used for a broad range of applications including, for example, chromatography (e.g., affinity, gas, ion exchange, reverse-phase, normal-phase), assays, proton sponges, catalysis, concentration of trace materials and the like. Further, the capturing can be an end in itself (e.g., removing a contaminant from a mixture) or it can be a step in a multistep process (e.g., recovering an analyte from a mixture).

In a preferred embodiment, the capturing comprises a step in an assay. Presently preferred assays include members selected from the group consisting of competitive assays, sandwich assays, agglutination assays and combinations thereof.

In another preferred embodiment, the capturing comprises a step in a method of purifying a molecule from a mixture of molecules. In this embodiment, the other molecules will typically be separated from the captured molecule by a method such as washing with an appropriate solvent, vapor or gas (e.g., gas chromatography), centrifuging a suspension comprising the particles and the like. Thus, in a preferred embodiment, the method further comprises washing the multilayered material-molecule complex with a solvent for those components of the mixture that are not captured.

Any molecule having a complementary recognition moiety, wherein the recognition moiety can be tethered to the particulate material of the invention can be captured using this method. In a preferred embodiment, the molecule captured is a member selected from the group consisting of antibodies, antigens, carbohydrates, nucleic acids, enzymes, enzyme substrates, peptides and combinations thereof.

To further enable the practice of this aspect of the invention, in a fifth aspect, the invention provides a device for capturing a molecule comprising:
  (a) a multilayered material comprising;
    a particulate substrate;
    a metal film layered onto the substrate;

an organic layer attached to the metal film; and a recognition moiety attached to a member selected from the group consisting of the organic layer, the metal film and combinations thereof, wherein the recognition moiety associates with the molecule forming a multilayered material-molecule complex, thereby capturing the molecule; and (b) a means to contain the multilayered material.

In a preferred embodiment, the particulate substrate comprises silica. In a further preferred embodiment, the metal film comprises gold. In a still further preferred embodiment, the organic layer comprises an organosulfur moiety. In yet another preferred embodiment, the recognition moiety is a member selected from the group consisting of biomolecules, organic groups, metal chelates and organometallic moieties.

The means to contain the multilayered material can have substantially any configuration and choosing an appropriate configuration for a particular application is well within the abilities of those of skill in the art. In certain preferred embodiments, the means to contain comprises a member selected from the group consisting of wells, columns, tubes and combinations thereof.

G.2 Affinity Chromatography

Affinity chromatography enables the efficient isolation of species such as biological molecules or biopolymers by utilizing their recognition sites for certain supported chemical structures with a high degree of selectivity. Previous affinity chromatographic methods have utilized materials of varying chemical structure as supports. For example, agarose gels and cross-linked agarose gels have been the most widely used support materials. Their hydrophilicity makes them relatively free of nonspecific binding, but their compressibility makes them less attractive as carriers in large scale processing, such as in manufacturing. Controlled-pore glass (CPG) beads have also been used in affinity chromatography. Although high throughputs can be obtained with columns packed with CPG, this carrier is even more expensive than agarose beads. Cellulose particles have also been used by immunochemists for synthetic affinity sorbents. However, compared to agarose gels, cellulose particles are formed with more difficulty and therefore, have received less attention in the preparation of affinity sorbents for enzymes. Cellulose, however, is perhaps the least expensive of all support matrices. Two lesser-used support matrices are polyacrylamide gel beads and Sephadex™ gel beads made from dextran and epichlorohydrin. Although convenient methods have been developed for using them, the softness of these beads yields poor column packings, and their low molecular porosity yields a sorbent with poor ligand availability to the ligate.

A review of current affinity chromatographic matrices, leads to the conclusion that there exists a need for a support and method useful both for ion exchange and affinity chromatography-based purification which will have high stability, high porosity, low non-specific adsorption, high flow rate, non-compressibility, controlled gelation, and which will be useful for both laboratory and industrial-scale biological separations. It is at the industrial level of manufacturing, especially, where the aforementioned drawbacks of the prior art have had their most important effect and where this need is the strongest.

Thus, in a sixth aspect, the present invention provides a method for isolating a molecule from other molecules by affinity chromatography comprising:

(a) contacting the molecule with a plurality of multilayered particles, the particles comprising;

a particulate substrate;

a metal film layered onto the substrate;

an organic layer attached to the metal film; and a recognition moiety attached to a member selected from the group consisting of the organic layer, the metal film and combinations thereof;

(b) forming a complex between the recognition moiety and the molecule, thereby forming a plurality of particle-molecule complexes; and (c) washing the plurality of particle-molecule complexes with a solvent for the other molecules.

Following the purification, it will often be desirable to remove the purified molecule from the chromatographic matrix. Thus, in a preferred embodiment, the method of the invention further comprises disrupting the complex between the recognition moiety and the molecule, thereby separating the molecule from the particle.

Although it is within the scope of the present invention to utilize the affinity chromatographic method for the purification of any member of any class of molecules, in a preferred embodiment, the molecule being purified is a biomolecule. In further preferred embodiments, the biomolecule is a member selected from the group consisting of peptides, enzymes, enzyme substrates, carbohydrates, nucleic acids, antibodies, antigens and combinations thereof.

The choice of appropriate recognition groups for performing a particular affinity chromatographic separation will be apparent to those of skill in the art, however, in preferred embodiments, the recognition moiety is a member selected from the group consisting of biomolecules, organic groups, metal chelates, organometallic moieties and combinations thereof.

The consideration concerning the particulate core of the material are generally the same as those discussed above. The particle size of the particulate is not critical but influences somewhat the flow rate at which the sample to be treated passes through the material. For radial flow applications, uniform particle sizes greater than about 5 microns are preferred, with about 10–100 microns constituting a practical operational range. Somewhat smaller particle sizes are possible for tangential flow applications where the sample flows across, and not through, the matrix material. The optimum amount of particulate material used will vary depending on the molecular separation desired.

The literature is replete with articles, monographs, and books on the subject of affinity chromatography, including such topics as affinity chromatography supports, crosslinking members, ligands and their preparation and use. A sampling of those references includes: "Affinity chromatography: general methods," *Methods Enzymol.*, 182: 357–71 (1990); "Novel affinity-based processes for protein purification,", Ferment, *Bioeng.*, 70(3): 199–209 (1990). "Applications of preparative high-performance liquid chromatography to the separation and purification of peptides and proteins," *J. Chromatogr.*, 492: 431–69 (1989); "Purification of enzymes by heparin-Sepharose affinity chromatography," *J. Chromalogr.*, 184(3): 335–45 (1980); "Principles of multi-enzyme purification by affinity chromatography," *Enzyme Eng.*, 4: 441–2 (1978); "General ligand affinity chromatography in enzyme purification; Ligands, affinity chromatography, enzyme purification," *J. Macromol. Sci., Chem.*, A10(1–2): 15–52 (1976); "Affinity purification of enzymes," *Chem. Technol.*, 5(9): 564–71 (1975); "Bioaffinity chromatography," *Pract. High Perform. Liq. Chromatogr.*, 193–206 (1976); "Affinity chromatography of plasma proteins-an overview," *Proc. Int. Workshop Technol. Protein Sep. Improv. Blood Plasma Fractionation,*

422–3 5; (1977) "Affinity chromatography of enzymes," *Affinity Chromatogr., Proc. Int. Symp.* 25–38, (1977) (Pub. 1978); "Protein immobilization and affinity chromatography," *Biotechnol. Appl. Proteins Enzymes. Pap. Conf,* 83–102 (1976) (Pub. 1977); "Use of affinity chromatography in protein structure studies," *Pept., Proc. Eur. Pept. Symp.,* 11th, 203–22 (1971) (Pub. 1973); "Affinity chromatography of enzymes," *Fed. Eur. Biochem. Soc. Meet.,* [Proc] 30 (1974); and AFFINITY CHROMATOGRAPHY: A PRACTICAL APPROACH, IRL, Press Limited, Oxford England (1985). Those of skill in the art will have ample guidance in developing particular affinity chromatographic methods utilizing the materials of the invention.

To better illustrate this aspect of the invention, the following discussion, focusing on enzyme purification, is offered. The use of enzyme purification is intended to be illustrative and not limiting.

The starting point for designing an affinity matrix for removal of specific enzymes is to examine the structure of the enzyme and, particularly, the structure of the inhibitors of the enzymes. The complex formed between an enzyme and its inhibitor provides the best picture of how the enzyme may interact with the specific protein structure. Enzyme inhibition is always competitive and reversible as expressed by the following equation:

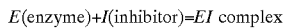

$E(\text{enzyme}) + I(\text{inhibitor}) = EI$ complex

In affinity chromatography, this reaction between enzyme and the affinity matrix-bound inhibitor or substrate is used to selectively extract the enzyme from crude solutions, either as a batch or continuous process. After washing away the contaminating proteins, the enzyme is freed from the matrix by introducing free ligand, which competes with the matrix for binding to the enzyme. The eluted enzyme is freed of inhibitor by dialysis or ultrafiltration techniques, or in the case of potent inhibitors by chemical processes that interfere with binding to the inhibitor.

The affinity matrix is typically packed in a cylindrical column to permit a continuous flow process, although batch operation are a reasonable alternative for extracting the enzyme from crude preparations. The affinity column can be protected by a guard column of native supporting matrix (e.g. Sepharose CL-4B) to filter out proteins that bind non specifically to the matrix and would be difficult to wash away completely from the bound enzyme.

Both columns are typically equilibrated with a buffer at neutral pH prior to application of the enzyme solution, for which 3 or more column volumes is regarded as sufficient. Any nonreactive compound with a pKa near neutrality is satisfactory. Quite often a buffer such as N-[2-hydroxyethyl] piperazineN'-[2-ethanesulfonic acid] (HEPES) proves to be satisfactory. Other components can be included in the buffer, such as sucrose, 3-[3-cholamidopropyl)dimethylammonio]-1-propanesulfonate (CHAPS) to slow the rate of dissociation of enzyme having multiple subunits to inactive monomers. Other useful buffer solutions and additives for a given purpose will be apparent to those of skill in the art.

The flow rate through the column can vary over a wide range. An important consideration in the choice of flow rates is the rate constant for association and dissociation of the inhibitor and the enzyme. When the rates of association are slower than normal, slow flow rates are generally used (e.g., flow rate equivalent to ¼ bed volume per hour)

Following its immobilization on the affinity matrix, the bound enzyme is generally washed with buffer to remove the last traces of contaminating proteins. Extensive washing, using as much as 20 column volumes of buffer, is desirable and generally leads to no detectable loss during this process.

After washing, the enzyme is eluted from the matrix by including the free ligand, or another inhibitor or substrate for the enzyme in the wash buffer. Again, the rate constants for equilibration with particular inhibitors require special consideration. The half-life for dissociation of the inhibitor or substrate can be used as a guide for ascertaining appropriate flow rates. If the rates are too slow to use continuous flow to elute the enzyme, elution is accomplished in a batch process, in which the column is flooded with free ligand and then incubated for a period (e.g., overnight) to allow the exchange to reach equilibrium before restarting the flow to elute the enzyme.

Lastly, purified enzyme must be separated from the E-I complex. At this point, the purified enzyme is complexed with the eluting ligand. Removal of the ligand and reactivation of the enzyme is classically accomplished by dialysis or diafiltration. Similar methods are available for purification of other biomolecules.

In a variation on this method, the enzymes can be utilized as components of the affinity matrix to isolate the components to which they bind.

Of particular interest is the immobilization of enzymes such as hydrolases, isomerases, proteases, amylases, and the like. These immobilized enzymes can then be used in biochemical reactors, as is otherwise well known in the art. In still other preferred embodiments, these enzymes are immobilized onto magnetic particles of the invention to allow their separation from the synthesis milieau.

Antibodies can be similarly isolated by the use of a matrix having bound thereto one or more species recognized by the antibody. Alternatively, antibodies can be used e.g. in an affinity matrix (e.g. affinity column) to isolate the targets (e.g. antigen, receptor or receptor subunits) to which they bind. Briefly, in one embodiment, affinity chromatography involves immobilizing (e.g. on the particulate material of the invention) one or more species of antibodies. The members of an array of molecules (e.g., small molecular drugs, peptides, peptide mimetics, nucleic acids, etc.), cells, cellular lysate, or cellular homogenate are then contacted with the immobilized antibody which then binds to its cognate ligand. The remaining material is then washed away and the bound/isolated cognate ligand can then be released from the antibody for further use. Methods of performing affinity chromatography are well known to those of skill in the art (see, e.g., U.S. Pat. Nos.: 5,710,254; 5,491,096; 5,278,061; 5,110,907; 4,985,144; 4,385,991; 3,983,001, etc.).

It is now known that for the coupling of a biomolecule or a ligand for a biomolecule to a solid matrix, to have maximum affinity for a binding partner, it is important that the ligand or biomolecule retain its active conformation after coupling to the matrix. For example, antibody molecules exist in their active forms only in a small number of conformations. The functional affinities vary widely upon coupling to a solid surface. Thus, the noncovalent interactions between the matrix and ligand with forces such as hydrogen bonding and hydrophobic interactions have manifest influence on antibody conformations. Since antibodies are bulky in structure, the physical character of the matrix, such as surface area and pore distribution, also is a consideration from a steric hindrance point of view. For example, it has been found that above the level of about 3–4 mg/gm of IgG bound to Sepharose™, additional bound IgG is ineffective as a ligand. Apparently, as higher levels of IgG are coupled to the Sepharose™, antibody activity actually diminishes due to crowding of IgG, preventing the action of the antibody. As a solution to this problem, the present invention provides a material in which the concentration and spacing of the bound antibody, or other molecule, can be rationally controlled and varied to optimize the separation parameters.

Typical ligands of use in this aspect of the invention include, but are not limited to, DNA blood type antigen, anti-alpha feto protein, C1Q, protein A, protein G, polylysine, mucopolysaccharides such as heparin, methylated albumin, tryptophan, phenylalanine, concavaline A, and the like. For removal of proteolytic enzymes from IgG, episilonaminoacrylic acid, lysine, methyl-p-aminocyclohexane carboxylic acid, and trasylol, potential inhibitors, are preferred. For removal of mucopolysaccharides such as heparin, low molecular weight basic proteins (protamines) such as protamine sulfate are preferred. For removal of kallikrein and PKA, benzamidine is effective. For removal of endotoxins, polymyxin-B-sulfate is preferred.

Preferred particulates which can be used include all of those substances which can be provided in finely divided form. Mixtures of such compositions may also be utilized. Exemplary of such particulates are silica, alumina, zirconium oxide, diatomaceous earth, perlite, clays such as vermiculite, carbon such as activated carbon, modified polymer particulates such as other ion-exchange resins, crystalline cellulose, molecular sieves, and the like, the surfaces of which may be modified in a conventional manner. Such materials are commercially available under a variety of trademarks such as Biosila™, Hi-Flosil™, Li Chroprep Si™, Micropak Si™, Nucleosil™, Partisil™, Porasil™, Spherosil™, Zorbaxcil™, Corasil™, Pallosil™, Zipax™, Bondapak™, LiChrosorb™, Hypersil™, Zorbax™, Perisorb™, Fractosil™, Corning Porous Glass™, DoWeX™, Amberlite™ resins, and the like.

As will be recognized by one skilled in the art, ligands suitable for the practice of the present invention include all ligands which may be immobilized by the affinity matrix and still maintain biological activity, such ligands being represented by, but not limited to, the following general classes: amino acids; avidin-biotins; carbohydrates; glutathiones; hydrophobic matrices; immunoglobulins; insoluble proteins; lectins; nucleotides; polyamino and polynucleic acids; and specialty ligands.

Typical amino acids suitable as affinity ligands include L-alanine, L-arginine, L-asparagine, L-aspartic acid, L-cysteine, L-cystine, L-glutamic acid, L-glutamine, glycine, L-histidine, L-isoleucine, L-lysine, L-methionine, L-phenylalanine, L-proline, L-serine, L-threonine, L-thyroxine, D-tryptophan, L-tryptophan, L-tyrosine and L-valine.

Typical avidin-biotin ligands include avidin, biotin, desthiobiotin, diaminobiotin, and 2-iminobiotin.

Typical carbohydrates include the glucosamines, the glycopryranoses, the glactosamines, the fucosamines, the fucopyranosylamines, the galactosylamines, the glycopyranosides, and the like.

Typical glutathione ligands include glutathione, hexylglutathione, and sulfobromophthalein-S-glutathione.

Typical hydrophobic matrices include amino allyl, butyl, decyl, dodecyl, ethyl, hexyl, methyl, octyl, pentyl, phenyl and propyl.

Typical immunoglobulins include the IgG's, including anti-goat IgG, anti-human IgG, anti-mouse IgG, anti-rabbit IgG, goat IgG, human IgG, rabbit IgG, and anti-glucose-6-phosphate dehydrogenase.

Typical proteins include factor VIII von Willebrand factor complex (VIII:C/VIII:RP complex); factor VIII procoagulant activity protein (VIII:C); von Willebrand factor (VIII:RP) (see, U.S. Pat. No. Re. 32,011); factor IX; vitamin K dependent clotting factors such as X, VII, II, protein C, and protein S; antithrombin III; tissue factor inhibitor; plasminogen activator inhibitor; tissue plasminogen activator; erythropoietin; colony stimulating factors; growth factors; protein C inhibitor; interluekins; labeled proteins; DNA probes; interferons; hepatitis vaccine; lipocordons; or any protein, peptide, or fragment to which a monoclonal antibody can be made or bound. The source of proteins such as VIII:C, VIII:RP and factor IX may be plasma or a recombinant source.

Typical insoluble proteins include aprotinin, fetuin, gelatin, globin, glycophorin, hemoglobin, insulin, lactalbumin, parvalbumin, protamine, protein-A, protein-G, ribose-binding protein, and trypsin inhibitor.

Typical lactins, include Arachis hypogaea, concanavalin A, Dolichos biflorus, glycine max, Lens culinaris, Phytolacca americana, Pisum sativum, and the like.

Typical nucleotides include the adenosine mono- and diphosphates, the cytidine di- and triphosphates, flavin mononucleotide, the guanosine mono-, di-, and triphosphates, and the uridine mono-, di-, and triphosphates.

Typical polyamino and polynucleic acids include DNA, polyadenylic acid, polycytidylic acid, polylysine, polyriboadinylic, polyribocytidylic, polyriboguanylic, polyriboinosinic acid, and polyuridylic.

In a presently preferred embodiment, the affinity matrices of the invention are contained within a device such as a column, tube, microtiter plate and the like. Alternatively, the matrix can be supported on a structure such as a plate manufactured of, for example, glass or plastic.

In those embodiments in which the affinity matrices of the invention are configured within a device, the device can allow allows radial or tangential flow of sample. By "radial" flow is intended where the sample is passed through the affinity matrix. By "tangential" flow is intended where the sample flows across the surface, but not through the affinity matrix. Various proteins which can be isolated using conventional affinity chromatography support materials may be isolated using the method of the present invention.

G.3 Size Exclusion Chromatography

In a seventh aspect, the invention provides a method of isolating a first molecule from a second molecule by size exclusion chromatography, comprising:
(a) contacting the first and second molecule with a plurality of multilayered particles to form a mixture comprising the first molecule, the second molecule and the particles, the particles comprising;
    a particulate substrate;
    a metal film layered onto the substrate;
    a hydrophilic polymer attached to the metal film; and
(b) contacting the mixture with a solvent for both the first molecule and the second molecule.

In a presently preferred embodiment of this aspect of the invention, the hydrophilic polymer comprises poly (ethyleneglycol).

Size exclusion chromatography is a well-known methodology for separating molecules on the basis of differences in molecular size and/or weight. This form of chromatography is generally non-interactive. The support consists essentially of a porous network in which solute molecules are either retained in or excluded from based on their hydrodynamic volumes; that is their size and shape. See, for example, Yau el al., MODERN SIZE EXCLUSION CHROMATOGRAPHY, Wiley-Interscience, New York, 1979.

As a sample passes through the size exclusion matrix, the solute molecules are sorted by the pores in the packing material. Large molecules that cannot enter many of the pores pass through the matrix first. In contrast, small molecules will be able to enter many of the pores and will spend a comparatively longer time associated with the matrix. Between these two extremes, intermediate size molecules can enter some pores, but not others and, thus, spend an intermediate amount of time associated with the matrix.

In this aspect of the invention, the porous network is formed from hydrophilic polymers. The pore size and the density of the network on the particulate material can be adjusted by varying the size and the amount of the hydrophilic polymer bound to the surface. Because organosulfur monolayers on metal surfaces typically form without an "islanding" effect when more than one compound is used, an array of homogeneous matrices with novel structures and useful properties can be formed by mixing varying concentrations of, for example, thiol-PEGs of different lengths (i.e., molecular weights). Further, a polymer mixture including hydrophilic polymers of different structure and/or different molecular weights can be used to vary the characteristics of the matrix. The choice of appropriate matrix characteristics will be apparent and easily accessible to one of skill in the art.

G.4. Assays

Assays based on specific binding reactions have been used for detecting a wide variety of components such as drugs, hormones, enzymes, proteins, antibodies, and infectious agents in various biological fluids and tissue samples. In general, the assays consist of an analyte, a binding substance for the analyte, and a detectable label. Immunological assays involve reactions between immunoglobulins (antibodies) which are capable of binding with specific antigenic determinants of various compounds and materials (antigens). Other types of reactions include binding between avidin and biotin, protein A and immunoglobulins, lectins and sugar moieties and the like. See, for example, U.S. Pat. No. 4,313,734, issued to Leuvering; U.S. Pat. No. 4,435,504, issued to Zuk; U.S. Pat. Nos. 4,452,901 and 4,960,691, issued to Gordon; and U.S. Pat. No. 3,893,808, issued to Campbell.

These assay techniques provide the ability to detect both the presence and amount of small quantities of analytes and are useful in, for example medical diagnostics and forensic applications.

Thus, in an eighth aspect, the present invention provides a method for determining the presence or amount of an analyte in a test sample comprising:
(a) contacting the test sample with a plurality of multi-layered particles, the particles comprising;
   a particulate substrate;
   a metal film layered onto the substrate;
   an organic layer attached to the metal film; and
   a recognition moiety attached to a member selected from the group consisting of the organic layer, the metal film and combinations thereof;
(b) forming a complex between the recognition moiety and at least a portion of the analyte, thereby forming a plurality of particle-analyte complexes; and
(c) detecting the analyte.

The method of detecting can utilize any art-recognized method of detecting the presence of a compound or a binding interaction. In a preferred embodiment, the analyte is labeled with a detectable label.

The detectable label is often necessary because the results of specific binding reactions are frequently not directly observable. A variety of detectable labels have been devised for determining the presence of a reaction. Detectable labels have involved well known techniques including radiolabeling and the use of chromophores, fluorophores and enzyme labels. Radiolabels can be detected by radiation detectors. Chromophores and fluorophores have been detected by use of spectrophotometers or the naked eye. Redox active groups can be detected by electroanalytical methods. Biotin can be detected by its well-know binding to avidin or strepavidin. The avidin or strepavidin can itself be labeled with any of the labels described herein. Where members of a specific binding pair are tagged with an enzyme label, their presence may be detected by the enzymatic activation of a reaction system wherein a compound such as a dyestuff, is activated to produce a detectable signal.

Thus, in preferred embodiments, the label is a member selected from the group consisting of fluorescent groups, chromophoric groups, radioactive groups, redox active groups, biotin, enzyme labels and combinations thereof.

The labels in the present invention can be primary labels (where the label comprises an element which is detected directly) or secondary labels (where the detected label binds to a primary label, e.g., as is common in immunological labeling). An introduction to labels, labeling procedures and detection of labels is found in Polak et al., INTRODUCTION TO IMMUNOCYTOCHEMISTRY, $2^{nd}$ Ed., Springer Verlag, NY, (1977), and in Haugland, HANDBOOK OF FLUORESCENT PROBES AND RESEARCH CHEMICALS, a combined handbook and catalogue Published by Molecular Probes, Inc., Eugene, Oreg.(1996)

Primary and secondary labels can include undetected elements as well as detected elements. Useful primary and secondary labels in the present invention can include spectral labels such as fluorescent dyes (e.g., fluorescein and derivatives such as fluorescein isothiocyanate (FITC) and Oregon Green™, rhodamine and derivatives (e.g., Texas red, tetrarhodimine isothiocynate (TRITC), etc.), dixogenin, biotin, phycoerythrin, AMCA, CyDyes™, and the like), radiolabels (e.g., $^3$H, $^{125}$I, $^{35}$S, $^{14}$C, $^{32}$P, $^{33}$P, etc.), enzymes (e.g., horse-radish peroxidase, alkaline phosphatase etc.) spectral colorimetric labels such as colloidal gold or colored glass or plastic (e.g. polystyrene, polypropylene, latex, etc.) beads. The label can be coupled directly or indirectly to a component of the detection assay (e.g., a nucleic acid) according to methods well known in the art. As indicated above, a wide variety of labels can be used, with the choice of label depending on sensitivity required, ease of conjugation with the compound, stability requirements, available instrumentation, and disposal provisions.

In general, a detector which monitors an analyte is adapted to the particular label which is used. Typical detectors include spectrophotometers, phototubes and photodiodes, potentiostats, microscopes, scintillation counters, cameras, film and the like, as well as combinations thereof. Examples of suitable detectors are widely available from a variety of commercial sources known to persons of skill. Commonly, an optical image of an analyte comprising bound label is digitized for subsequent computer analysis.

Preferred labels include those which utilize 1) chemiluminescence (using, for example, Horseradish Peroxidase and/or Alkaline Phosphatase with substrates that produce photons as breakdown products) with kits being available, e.g., from Molecular Probes, Amersham, Boehringer-Mannheim, and Life Technologies/ Gibco BRL; 2) color production [using both Horseradish Peroxidase and/or Alkaline Phosphatase with substrates that produce a colored precipitate] [kits available from Life Technologies/Gibco BRL, and Boehringer-Mannheim]; 3) hemifluorescence using, e.g., Alkaline Phosphatase and the substrate AttoPhos [Amersham] or other substrates that produce fluorescent products, 4) fluorescence [e.g., using Cy-5 [Amersham], fluorescein, and other fluorescent tags]; 5) radioactivity using, for example, kinase enzymes or other end-labeling approaches, nick translation, random priming, or PCR to incorporate radioactive molecules into the labeling nucleic acid; 6) redox labels using, for example, amino drugs labeled with cationic cobalocenium, procationic ferrocene or nitroxide groups (Limoges et al., *J. Electroanal. Chemn.* 402: 175 (1996)), antibodies or enzymes labeled with ferrocene by reaction of n-(2-ferroceneethyl)maleimide with cysteine groups (Digleria et al. *FEBS Lett.* 390: 142 (1996), or 5-aminosalicylic acid as a redox-mediator for amperometric detection of enzymes labeled with horseradish peroxidase (Abdelhamid et al., *Electroanalysis* 10: 758 (1998). Other methods for labeling and detection will be readily apparent to one skilled in the art.

Fluorescent labels are highly preferred labels, having the advantage of requiring fewer precautions in handling, and being amenable to high-throughput visualization techniques (optical analysis including digitization of the image for analysis in an integrated system comprising a computer). Preferred labels are typically characterized by one or more of the following: high sensitivity, high stability, low background, low environmental sensitivity and high specificity in labeling. Fluorescent moieties, which are incorporated into the labels of the invention, are generally are known, including Texas red, dixogenin, biotin, 1- and 2-aminonaphthalene, p,p'-diaminostilbenes, pyrenes, quaternary phenanthridine salts, 9-aminoacridines, p,p'-diaminobenzophenone imines, anthracenes, oxacarbocyanine, merocyanine, 3-aminoequilenin, perylene, bis-benzoxazole, bis-p-oxazolyl benzene, 1,2-benzophenazin, retinol, bis-3-aminopyridinium salts, hellebrigenin, tetracycline, sterophenol, benzimidazolylphenylamine, 2-oxo-3-chromen, indole, xanthen, 7-hydroxycoumarin, phenoxazine, calicylate, strophanthidin, porphyrins, triarylmethanes, flavin and many others. Many fluorescent tags are commercially available from the SIGMA chemical company (Saint Louis, Mo.), Molecular Probes, R&D systems (Minneapolis, Minn.), Pharmacia LKB Biotechnology (Piscataway, N.J.), CLONTECH Laboratories, Inc. (Palo Alto, Calif.), Chem Genes Corp., Aldrich Chemical Company (Milwaukee, Wis.), Glen Research, Inc., GIBCO BRL Life Technologies, Inc. (Gaithersburg, Md.), Fluka Chemica- Biochemika Analytika (Fluka Chemie AG, Buchs, Switzerland), and Applied Biosystems (Foster City, Calif.), as well as many other commercial sources known to one of skill.

Most typically, the amount of analyte present is measured by quantitating the amount of label fixed to the material of the invention following a binding event. Means of detecting and quantitating labels are well known to those of skill in the art. Thus, for example, where the label is a radioactive label, means for detection include a scintillation counter or photographic film as in autoradiography. Where the label is optically detectable, typical detectors include microscopes, cameras, phototubes and photodiodes. Many other detection systems are widely available.

Immunological assays are of three general types. In competitive binding assays, labeled reagents and unlabeled analyte compounds compete for binding sites on a binding material. After an incubation period, unbound materials are washed off and the amount of labeled reagent bound to the site is compared to reference amounts for determination of the analyte concentration in the sample solution.

A second type of immunological assay is known as a sandwich assay and generally involves contacting an analyte sample solution to a surface comprising a first binding material immunologically specific for that analyte. A second solution comprising a labeled binding material of the same type (antigen or antibody) as the first binding material is then added to the assay. The labeled binding material will bind to any analyte which is bound to the first binding material. The assay system is then subjected to a wash step to remove labeled binding material which failed to bind with the analyte and the amount of labeled material remaining is ordinarily proportional to the amount of bound analyte.

A third type of immunological assay technique involves agglutination reaction techniques and is exemplified by well-known assays for blood antigens and serum types. Immunological cross-reactivity between antibodies within serum and antigens presented on red blood cell surfaces is indicated by the formation of a three dimensional cross-linked network of red blood cells and antibodies. The agglutination of the serum/red blood cell mixture results in the formation of a pellet which can be visible to the naked eye.

These assay procedures, enumerated above, were originally performed according to liquid phase immunochemistry techniques wherein enzymes and radiolabeled reactions were carried out in liquid solution in apparatus such as microtiter plates. More recently, techniques and procedures have been adapted for carrying out "solid" phase assays wherein enzymatic and immunological reactions are carried out in solution on immobilizing substrates. The particulate material of the invention are well suited for use as an immobilizing substrate.

These types of assays, generally designated immunochromatographic immunoassays, can be developed in any number of formats employing principals of competitive, sandwich, or agglutination types of assays. They can also involve either flow across or flow along the immobilizing substrate. In general, the sandwich assays have the greatest utility for detection of large protein analytes or antibodies. The flow across type of assays have been used most extensively in sandwich type assays.

An exemplary immunochromatographic sandwich immunoassay procedure using the particulate material of the invention employs a porous surface and multilayered particles with an attached agent such as polystyrene latex spheres, natural or synthetic dyes, or metal sol particles such as colloidal gold, as visual labels which in the presence of a suitable solvent can diffuse through or across a porous surface. One member of a binding pair is adsorbed or bound to the surface of the particles either through covalent or noncovalent attachment.

The porous surface is generally a flat sheet and is usually comprised of either nylon, nitrocellulose, glass fiber, or the like. In a typical immunochromatographic format a region or small area of the porous surface becomes a solid phase capturing surface by immobilizing a member of a binding pair directly onto the surface of a porous membrane or by indirectly attaching the member onto capture particles (i.e., latex, glass,) which are immobilized on the surface of a porous membrane. Direct immobilization of the binding pair to a porous membrane or capture particles occur through electrostatic interaction, (i.e., differences in ionic charge), hydrophobic interaction, or covalent binding. Where capture particles are used the immobilization of capture particles to porous membranes can also occur through the same phenomena or through size exclusion preventing migration of the particles through the pores or fibers of the membrane. Many other types of assays can be run utilizing the particles of the invention.

In a typical noncompetitive immunochromatographic assay, a test sample of a biological fluid such as blood, serum, plasma, saliva, urine, etc. must be in a sufficient volume and have a sufficient concentration of analyte to allow for sufficient interaction to occur between the analyte of interest, the labeled particles and the capturing solid phase. In order to increase the reaction kinetics, the concentration of particle labeled member of a binding pair and the concentration of binding pair at the surface of the porous membrane or capturing particles is optimized to produce as much specific binding as possible and at the same time minimize any nonspecific binding. The concentration of the particle labeled member must be of a concentration that does not produce prozone phenomena throughout the range of analyte concentrations that are of interest. Such concentration optimization is well within the abilities of one of skill.

Immunochromatographic assays can be in the form of strips or layers of the multilayered materials of the invention employing a hydrophobic support (e.g., Mylar, polystyrene, polypropylene, glass, etc.) wherein the multilayered material of the invention is either fixed directly or indirectly with a binder such as glue to the support.

Hydrophobic supports and housings can be employed to reduce evaporation of the fluid phase while the immunoreactants are being brought into contact with each other.

In an exemplary non-competitive assay in accordance with this aspect of the invention, an analyte is solubilized, deposited and bound onto the particulate material. The particulate material is then hydrated and sequentially exposed to primary antibodies and enzyme-conjugated secondary antibodies specific for the primary antibodies, with washing steps in between where appropriate. Enzyme levels are then determined by, for instance, substrate conversion protocols well known in the art, and the amount of primary antibodies can thus be measured by reference to a standard run in parallel.

Additionally, a binding domain of a receptor, for example, can serve as the focal point for a drug discovery assay, where, for example, the receptor is immobilized, and incubated both with agents (i.e., ligands) known to interact with the binding domain thereof, and a quantity of a particular drug or inhibitory agent under test. The extent to which the drug binds with the receptor and thereby inhibits receptor-ligand complex formation can then be measured. Such possibilities for drug discovery assays are contemplated herein and are considered within the scope of the present invention. Other focal points and appropriate assay formats will be apparent to those of skill in the art.

In addition to ascertaining a binding event, it is frequently desired to quantitate the magnitude of the affinity between two or more binding partners. Thus, it is also within the scope of the present invention to utilize the particulate material disclosed herein as a support for such assays.

Thus, in an ninth aspect, the present invention provides a method of detecting or quantifying binding affinity between a first binding partner and a member PATENT selected from the group consisting of a recognition moiety, a second binding partner and combinations thereof, the method comprising:

(a) contacting a member selected from the group consisting of the first binding partner and a first binding partner-second binding partner complex with a plurality of multilayered particles, the particles comprising;

a particulate substrate;
a metal film layered onto the substrate;
an organic layer attached to the metal film; and
a recognition moiety attached to a member selected from the group consisting of the organic layer, the metal film and combinations thereof;

(b) forming a plurality of particle-first binding partner complexes; and (c) measuring the affinity.

In a preferred embodiment, the assay further comprises contacting the plurality of particle-first binding partner complexes with the second binding partner to form a population of first binding partner-second binding partner complexes. This typically results in the formation of a new population of free recognition moieties as the first binding partner is competitively removed from the recognition moiety.

In a further preferred embodiment, the affinity is measured by quantifying a population selected from the group consisting of first binding partner-second binding partner complexes, first binding partner, second binding partner, particle-first binding partner complexes, free recognition moieties and combinations thereof.

In a still further preferred embodiment, the first binding partner, the second binding partner and the recognition moiety are members independently selected from the group consisting of carbohydrates, antibodies, antigens, peptides, nucleic acids, enzymes, enzyme substrates, organic groups, metal chelates and organometallic moieties.

The format of an assay for extracting affinity data for two molecules can be understood by reference to an embodiment in which a ligand that is known to bind to a receptor is displaced by an antagonist to that receptor. Other variations on this format will be apparent to those of skill in the art. The competitive format is well known to those of skill in the art. See, for example, U.S. Pat. Nos. 3,654,090 and 3,850,752.

The binding of an antagonist to a receptor can be assayed by a competitive binding method using a ligand for that receptor and the antagonist. The binding assay can be performed, for example, in a 96-well filtration plate assembly (Millipore Corporation, Bedford, Mass.) containing the multilayered particulate material. One of the three binding partners (i.e., the ligand, antagonist or receptor) is bound to the particulate material. In an exemplary embodiment, the receptor is bound to the particulate material.

Various concentrations of unlabeled ligand can be added to different wells. A labeled antagonist is then applied to each well to a chosen final concentration. The mixtures will generally be incubated at room temperature for a preselected time. The receptor-bound labeled antagonist can be separated from the unbound labeled antagonist by filtration, washing or a combination of these techniques. Bound label remaining on the particulate material can be measured as discussed above. A number of variations on this general experimental procedure will be apparent to those of skill in the art.

Competition binding data can be analyzed by a number of techniques, including nonlinear least-squares curve fitting procedure. When the ligand is an antagonist for the receptor, this method provides the IC50 of the antagonist (concentration of the antagonist which inhibits specific binding of the ligand by 50% at equilibrium). The IC50 is related to the equilibrium dissociation constant (Ki) of the antagonist based on the Cheng and Prusoff equation: Ki=IC50/(1+L/Kd), where L is the concentration of the ligand used in the competitive binding assay, and Kd is the dissociation constant of the ligand as determined by Scatchard analysis. These assays are described, among other places, in Maddox et al., *J. Exp Med.,* 158: 1211 (1983); Hampton el al., SEROLOGICAL METHODS, A LABORATORY MANUAL, APS Press, St. Paul, Minn., 1990.

G.5. Preparation of Mulilayered Particles

In a tenth aspect, the present invention also provides a method of making the multilayered particulate material of the invention. The method comprises, (a) contacting a particulate substrate with a metal plating solution to form a particle having a metal film layered thereon;

(b) contacting the particle having a metal film layered thereon with a plurality of organic molecules that associate with the metal film.

Any metal that can be electrolessly plated onto a particle is useful in this aspect of the invention. Metals that are presently preferred as coatings include, but are not limited to, gold, silver, platinum, palladium, nickel and copper, more preferably gold and silver, and even more preferably, gold. In one embodiment, more than one metal is used. The more than one metal can be present as an alloy or they can be formed into a layered "sandwich" structure, or they can be laterally adjacent to one another.

Any electroless plating solution that can plate a metal onto a particle can be used in practicing this aspect of the invention, however, solutions having certain characteristics are presently preferred. In a presently preferred embodiment, the plating solution comprises an easily reduced metal salt. In a preferred embodiment, a gold plating solution is utilized and the gold plating solution comprises a reducible gold salt. A presently preferred reducible gold salt is $Na_3Au(SO_3)_2$.

In another preferred embodiment, the metal plating solution further comprises a reducing agent. Reducing agents that are useful in this aspect of the invention include, hydroxylamine, oxalic acid, hydrazine, sodium borohydride and formaldehyde. A presently preferred reducing agent is formaldehyde.

The metal film can be plated directly onto the particulate substrate, however, in a preferred embodiment, the method further comprises, prior to step (a), contacting a particulate substrate with a sensitizer to form a sensitized particulate substrate. In a preferred embodiment, the sensitizer is a transition metal salt. In a still further preferred embodiment, the sensitizer is salt of $Sn^{+2}$.

Sensitizers are desirable for adjusting the surface character of the particles. For example, it is known that, during the plating process, colloidal silica tends to aggregate or agglomerate when silver is electrolessly deposited. If the silica surface is first coated with, for example a complex oxide or a metal that forms a silicate (e.g., tin), the fine particles do not agglomerate. In certain preferred embodiments, it is desired that the particles do agglomerate. Thus, one method of achieving such agglomeration is to eliminate the sensitizing step.

In preferred embodiments, the metal salts used are soluble in water. Thus, salts such as metal chlorides, sulfates, nitrates, acetates and the like are particularly preferred. In other embodiments, the metal ion is complexed with an agent such as EDTA, tartrate and the like. The use of salts that are insoluble in water, but soluble in, for example, organic solvents (e.g. alcohols, DMSO, DMF, ethers, etc.), acids, bases and the like are also within the scope of the present invention.

In yet another preferred embodiment, when the outermost layer comprises gold, the method further comprises, prior to step (a), contacting the sensitized particulate substrate with a silver solution to form a silver coated particle. A presently preferred silver solution comprises $AgNO_3$. In a further preferred embodiment, the silver solution further comprises ammonia.

In certain preferred embodiments, a silver coated particle is produced which is not then advanced to the gold plating stage. Silver coated particles are useful when the particulate material is used in combination with elevated temperatures, particularly when the organic layer comprises an organosulfur moiety: the silver-sulfur bond has been found exhibit enhanced stability relative to the gold-sulfur bond at elevated temperatures. This embodiment will find use in, for example, using the particulate material as a synthesis support or an immobilizing medium for enzymes during enzymatic mediated synthesis at elevated temperatures.

Any particulate material or material which can be formed into a particle is an appropriate substrate for use in the present invention. Certain preferred substrates include particles that are members selected from silica particles, alumina particles and carbohydrate particles. Other useful particles are discussed above.

As discussed above in the context of other aspects and embodiments of the invention, an array of organic layers can be used to practice this aspect of the invention. A preferred organic layer comprises an organosulfur moiety. In another preferred embodiment, the organic layer comprises a moiety selected from the group consisting of recognition moieties, reactive moieties, protected reactive moieties and combinations thereof.

When the organic layer comprises a reactive moiety, in a preferred embodiment, the method further comprises as step (d), reacting the reactive moiety with a recognition moiety. In another preferred embodiment, when the organic layer comprises a protected reactive moiety and the method further comprises, (d) deprotecting the protected reactive moiety to form a reactive moiety; and (c) reacting the reactive moiety with a recognition moiety. Many protecting groups and methods of attaching protecting groups to, and removing them from, reactive groups are known to those of skill in the art and one of skill will be able to ascertain appropriate groups and experimental conditions for a particular application.

G.5a Morphology

The particulate materials can be used in a wide range of forms. For, example, the particles of the present invention can be utilized as powders comprising a collection of free flowing single particles. Alternatively, the particles can be formed into larger particles, or even monolithic formats, by methods such as pressing, molding, cross-linking and the like. Further, the particles can be layered onto a planar or curved substrate and bound thereto, producing a material analogous to a thin-layer chromatography plate. The particles can also be a constituent of an aerogel.

The particles produced by the methods described herein are generally free-flowing powders and are quite suitable for use as chromatographic media, solid supports for synthesis and assays and the like. In certain embodiments, the particles will be agglomerated into larger structures having a range of sizes, densities and levels of particle agglomeration. Methods for chemically cross-linking the particles are substantially similar to those described, spura, in the context of linking recognition moieties to the particles. The cross-linking can be used to simply increase the size of the particles or, alternatively, it can be utilized to introduce a porous characteristic to the cross-linked material for molecular capture, size exclusion applications and the like.

Methods of physically pressing metal coated particles are know in the art and both cold and warm pressing techniques are useful in practicing this embodiment of the present invention. See, for example, U.S. Pat. No. 4,944,985, issued to Alexander et al., on Jul. 31, 1990.

The materials of the invention can also be formed into aerogels. Aerogels are useful in catalysis and detection and have interesting thermal and optical properties. Additionally, aerogels are used to collect and concentrate ambient trace materials (i.e., cosmic dust, see, Tsou et al., *LPSC* 19:1205 (1988)). Aerogels are characterized by accessible, cylindical, branched mesopores. Owing to their high porosity and low density aerogels are unique materials. Aerogels are typically formed by the controlled condensation of small (polymeric or colloidal) particles. Agglomeration of the particles is controlled by chemical processes, usually the sol-gel process. The use of this process to form aerogels is well-known in the art. See, for example, Husing, et aL, *Angewandte Chemie* (*International Edition in English*), 37: 23–45 (1998), and references therein.

Appropriate methods for producing acrogels include, supercritical drying of liquid from a wet gel comprising the particulate material of the invention. In this embodiment, a solvent containing the particulate material is put into its supcrcritical state. Typically, the wet gel is placed in an autoclave and covered with additional solvent. After the autoclave is closed, the temperature is slowly raised resulting in an increase in pressure. Both the temperature and the pressure are adjusted to values above the supercritical point of the solvent and kept there for a period of time. Once the autoclave is completely filled with the solvent, the solvent is then slowly vented at constant temperature, resulting in a pressure drop. When ambient pressure is reached, the autoclave is cooled to room temperature and opened. Preferred solvents include, alcohols, acetone, 2-propanol, carbon dioxide and water.

G.6. Synthesis Supports

The particles of the invention can also be used as a solid support for a variety of syntheses. The particles are useful supports for synthesis of small organic molecules, polymers, nucleic acids, peptides and the like. See, for example, Kaldor et al., "Synthetic Organic Chemistry on Solid Support" In, COMBINATORIAL CHEMISTRY AND MOLECULAR DIVERSITY IN DRUG DISCOVERY, Gordon et al., Eds., Wiley-Liss, N.Y., 1998.

In an eleventh aspect, the present invention provides a method for assembling a compound, comprising:

(a) adding a first component of the compound to a first multilayered material comprising;
   a particulate substrate;
   a metal film layered onto the substrate;
   an organic layer attached to the metal film;
(b) adding a second component of the compound to the first multilayered material;
(c) reacting the first component and the second component to form a first product.

In this aspect, the particulate material is used as a solid phase synthesis support. Such supports and methods of using them are well known in the art. Solid supports are widely used to prepare, peptides, nucleic acids, oligosaccharides and small organic molecules, for example. See, Hernkens et al., *Tetrahedron,* 52: 4527–4554 (1996); Leznoff et al., *Acc. Chem. Res.,* 11: 327–333 (1978); Frechet et al., *J. Am. Chem. Soc.,* 86: 5163–5165 (1971); Kick et al., *J. Med Chem.,* 38: 1427–1430 (1995); Atherton et al., SOLID-PHASE PEPTIDE SYNTHESIS: A PRACTICAL APPROACH, IRL, Oxford, UK, 1989.

In this aspect, one compound can be prepared using one or a plurality of particles. Alternatively, an array of compounds can be synthesized and, preferable screened utilizing the particles of the invention. Further, the addition of components can be repeated using the same or different components as necessary to assemble the desired compound.

G.7. Combinatorial Arrays

Parallel, or combinatorial, synthesis has as its primary objective the generation of a library of diverse molecules which all share a common feature, referred to throughout this description as a scaffold. By substituting different moieties at each of the variable parts of the scaffold molecule, the amount of space explorable in a library grows. Theories and modern medicinal chemistry advocate the concept of occupied space as a key factor in determining the efficacy of a given compound against a given biological target. By creating a diverse library of molecules which explores a large percentage of the targeted space, the odds of developing a highly efficacious lead compound increase dramatically.

Parallel synthesis is generally conducted on a solid phase support, such as a polymeric resin. The scaffold, or other suitable intermediate is cleavably tethered to the resin by a chemical linker. Reactions are carried out to modify the scaffold while tethered to the multilayered particle. Variations in reagents and/or reaction conditions produce the structural diversity which is the hallmark of each library.

In a preferred embodiment, the present invention provides a method for assembling an array of compounds comprising:

(a) contacting a first region of a substrate with a first component of a first compound and contacting a second region of a substrate with a first component of a second compound, wherein the substrate comprises a multilayered material according to the present invention;
(b) contacting the first region with a second component of the first compound and contacting the second region with a second component of the second compound;
(c) reacting the first and the second components to form a first and second product.

As used herein, the term "substrate," refers to a means to present, contain or anchor at least one particle. "Region," refers to a selected portion of the means to present, contain or anchor the at least one particle. By way of example, the particles can be contained in a 96 well microtiter plate, the titer plate being the substrate. Thus, in this embodiment, "a first region of a substrate" will generally refer to one well of a microtiter plate, although the microtiter plate can be conceptually divided into regions incorporating more than one well. In another example, the substrate is a collection of tubes (e.g., test tubes, centrifuge tubes), the collection forming the substrate. In this embodiment, "a first region of a substrate" will generally refer to a tube, or group of tubes, containing the particles. Other substrate formats will be apparent to those of skill in the art.

The sequential addition of components can be repeated as many times as necessary in order to assemble the desired library of compounds. Thus, it is within the scope of this embodiment, to add a third component of a first compound and a third component of a second compound and react these components with the tethered reaction product of the first and second components.

During the process of assembling the array, any number of solvents, catalysts and reagents necessary to effect the desired molecular transformations can be added before, concurrently or after the addition of the component.

Virtually any type of compound library can be synthesized using the method of the invention, including peptides, nucleic acids, saccharides, small and large molecular weight organic and inorganic compounds.

Further, it is within the scope of the invention to synthesize an array having any number of compounds. In a presently preferred embodiment, the libraries synthesized comprise more than 10 unique compounds, preferably more than 100 unique compounds and more preferably more than 1000 unique compounds.

In another preferred embodiment, the invention provides a method for assembling an array of n compounds, comprising:
(a) contacting n regions of a substrate with n first components of n compounds, wherein the substrate comprises a multilayered material of the invention;
(b) contacting the n regions with n second components of the n compounds; and
(c) reacting the first and the second components to form n products.

The consideration applicable to the above method of assembling a combinatorial library are generally applicable to this embodiment.

The nature of these libraries is better understood by reference to peptide-based combinatorial libraries as an example. The present invention is useful for assembling peptide-based combinatorial libraries, but it is not limited to these libraries. The particulate material of the invention can be used to synthesize libraries of essentially any molecular format that is amenable to synthesis on a multilayered particle, including small organic molecules, carbohydrates, nucleic acids, polymers, organometallic compounds and the like. Thus, the following discussion, while focusing on peptide libraries, is intended to be illustrative and not limiting.

Libraries of peptides and certain types of peptide mimetics, called "peptoids", are assembled and screened for a desirable biological activity by a range of methodologies (see, Gordon et al; *J. Med Chem.*, 37: 1385–1401(1994). For example, the method of Geysen, (*Bioorg. Med. Chem. Letters*, 3: 397–404 (1993); *Proc. Natl. Acad Sci. USA*, 81: 3998 (1984)) employs a modification of Merrifield peptide synthesis, wherein the C-terminal amino acid residues of the peptides to be synthesized are linked to solid-support particles shaped as polyethylene pins; these pins are treated individually or collectively in sequence to introduce additional amino-acid residues forming the desired peptides. The peptides are then screened for activity without removing them from the pins. The particulate material of the invention can be similarly formed and used as a solid support for the synthesis of peptide or other libraries.

Houghton, *Proc. Natl. Acad. Sci. USA*, 82: 5131 (1985); Eichler et al., *Biochemistry*, 32: 11035–11041 (1993); and U.S. Pat. No. 4,631,211) utilizes individual polyethylene bags ("tea bags") containing C-terminal amino acids bound to a solid support. These are mixed and coupled with the requisite amino acids using solid phase synthesis techniques. The peptides produced are then recovered and tested individually. Fodor et al., *Science*, 251: 767 (1991) described light-directed, spatially addressable parallel-peptide synthesis on a silicon wafer to generate large arrays of addressable peptides that can be directly tested for binding to biological targets. The particulate material of the invention can be utilized in a similar manner.

In another combinatorial approach, equally applicable to the particulate material of the invention, Huebner et al. (U.S. Pat. No. 5,182,366) utilized functionalized polystyrene beads divided into portions each of which was acylated with a desired amino acid; the bead portions were mixed together, then divided into portions each of which was re-subjected to acylation with a second desirable amino acid producing dipeptides, using the techniques of solid phase peptide synthesis. By using this synthetic scheme, exponentially increasing numbers of peptides were produced in uniform amounts which were then separately screened for a biological activity of interest.

Parallel synthesis of "small" molecules (non-oligomers with a molecular weight of 200–1000) was rarely attempted prior to 1990. See, for example, Camps. et al., *Annaks de Quimica*, 70: 848 (1990). Recently, Ellmann disclosed the solid phase-supported parallel (also referred to as "combinatorial") synthesis of eleven benzodiazepine analogs along with some prostaglandins and beta-turn mimetics. These disclosures are exemplified in U.S. Pat. No. 5,288, 514. Another relevant disclosure of parallel synthesis of small molecules may be found in U.S. Pat. No. 5,324,483. This patent discloses the parallel synthesis of between 4 and 40 compounds in each of sixteen different scaffolds. Chen et al. have also applied organic synthetic strategies to develop non-peptide libraries synthesized using multi-step processes on a polymer support. (Chen et al., *J. Am. Chem. Soc.*, 116: 2661–2662 (1994)). The methods of each of these disclosures can be practiced using the particulate material of the invention as a solid support.

G.7a Screening

Assays for evaluating the compounds synthesized on the multilayered particle of the present invention are well known in the art. Although one usually does not know a priori in which specific assays a particular compound or group of library compounds will have activity, a useful system for screening libraries of the format of that described in the present invention, to identify activities with respect to a wide variety of enzymes and molecular targets, is the so-called "lawn assay."

In a lawn assay, the library of multilayered particles is screened for the ability of compounds on the particles to affect the activity of an enzyme. Using the lawn assay, particles containing the active compounds are quickly and easily located merely by viewing zones of inhibition in a matrix. In one embodiment, the multilayered particles are contacted with a colloidal matrix, such as agarose. The compounds are linked to the particles by a cleavable linker and released, e.g., by exposure to light. As they slowly diffuse out of the multilayered particles, zones of high concentration of the compounds are created in the particles' immediate vicinity. The compounds contact enzyme contained in the matrix. Enzyme substrate is contacted with the matrix and reacts with the enzyme. Conversion of substrate to product is measured by monitoring a photometric change in the substrate, or in a coenzyme or cofactor involved in reaction. For example, the substrate can be fluorogenic, i.e., becoming fluorescent when converted to product. In this case, compounds that are active inhibitors of the enzyme reaction are detected as dark zones of inhibition. The less active, or inactive, compounds are contained in the lighter areas.

Using this assay, positive results from an assay of a combinatorial library can be detected very quickly. Furthermore, compound activity can be quantitated by e.g., comparing the sizes of zones of activity. Once zones of activity have been determined, the relevant particles at the center of the zones can be located and the active compounds on those particles identified. The lawn assay thus allows large libraries of compounds to be quickly and easily screened. Very little effort is required to array the multilayered particles or assay the compounds released from the particles.

In another embodiment, the lawn assay is used to determine compounds that bind to a target molecule, and thereby affect a detectable signal generated by a labeled ligand bound to the target molecule. This assay allows screening of compounds that, e.g., act as agonists or antagonists of a receptor, or that disrupt a protein:protein interaction. It also allows detection of binding to DNA, RNA, or complex carbohydrates. For example, neurokinin receptor binds to a 7-nitrobenz-2-oxa- 1,3-diazol-4-yl (NBD)-labeled peptide ligand. The labeled ligand has the following formula: PhCO-2,4-diaminobutyric acid(gamma-NBD)-Ala-D-trp-Phe-D-pro-Pro-Nle-$NH_2$. NBD is a fluorophore, and binding of the labeled ligand to the neurokinin receptor increases NBD's fluorescence. When a compound displaces the NBD-labeled ligand from the neurokinin receptor, fluorescence of the NBD fluorophore is reduced (Turcatti et al, *Biochemistry*, 34: 3972–3980 (1995)). A library of multilayered particles can be screened for compounds that, for example, bind to neurokinin receptor in a colloidal matrix using this method. Active compounds are found in zones of decreased fluorescence.

As another example, a radioligand (tritium or $^{125}$-labeled) can be used to screen for compounds binding to a receptor with the lawn assay by using Scintillation Proximity Assay beads (SPA™, Amersham Corp.) or scintillant coated plates (Flashplates™, Dupont NEN Research Products). Receptor is bound to SPA™ beads or to a Flashplate™ surface and radiolabeled ligand in a colloidal matrix is allowed to interact with the receptor. This interaction brings the radiolabel in close proximity with the scintillant and results in a scintillation signal. The signal can be detected using x-ray film, or other commercially available film that is specifically designed to detect tritium dependent scintillations. Compounds released into the matrix from the multilayered particles that bind to receptor and displace the radioligand reduce the scintillation signal, i.e., result in a zone of reduced scintillation. The receptor used in the assay can be e.g., membrane-bound, tethered to a solid phase, or solubilized.

When using the assay to find compounds that affect enzyme activity, it is advantageous to employ a substrate or product of the enzymatic reaction that generates a detectable signal. The difference in signal between the substrate and product should be significant. It is particularly preferred to use a substrate which generates little or no signal, and which converts to a product which generates a strong signal. If the substrate produces detectable signal which cannot be distinguished from that of the product, it can create background noise, thereby reducing the overall sensitivity of the assay. For this reason, non-fluorescent substrates that convert to fluorescent products, i.e., fluorogenic substrates, are preferred. One well known fluorogenic substrate is fluorescein diacetate, which converts to fluorescein in the presence of an esterase, such as carbonic anhydrase. Other fluorogenic substrates include 7-amino-trifluoromethyl coumarin (AFC), 4-trifluoromethylumbelliferyl (HFC), 7-amino-4-methylcoumarin (AMC) and 4-methoxy-2-naphthylamine (MNA).

Alternately, a fluorescent substrate can be used that converts to a product having different excitation and emission characteristics. By using band-pass filters, so that only the product is excited and detected, the substrate can be effectively screened out. An example of such a fluorescent substrate is peptidylaminomethylcoumarin, which is converted by an appropriate protease, such as thrombin, to free aminomethylcoumarin. The free aminomethylcoumarin excites and emits at different wavelengths than does the peptidyl-aminomethylcoumarin (Kawabata et al., *Eur. J. Biochen.*, 172: 17 (1988)).

It is also possible to use a substrate containing internally quenched fluorophores that become fluorescent when converted to product. Such quenching reactions are well known (Matayushi et al., *Science*, 247: 954 (1990)). For example, a peptide substrate can be produced having two fluorophores at opposite ends, one absorbing the fluorescence of the other. The substrate therefore emits a negligible amount of light. Upon cleavage of the peptide by a suitable protease, the absorbing fluorophore is released and no longer quenches the other fluorophore, resulting in an increase in fluorescence. One such substrate is 4(dimethylaminophenylazo)-benzoic acid (DABCYL)-Gabu-glu-arg-met-phe-leu-ser-phe-pro-5- [(2-aminoethyl)aminonaphthalene-1 sulfonic acid (EDANS), which when cleaved by an aspartyl protease (e.g., plasmepsin 11 of Plasmodium falcioarum) becomes fluorescent. In screening a library of aspartyl protease inhibitors using the lawn assay, those that are active inhibit cleavage of the substrate, allowing quenching to be maintained. Active compounds are found in dark zones of inhibition.

Fluorescence can be detected, e.g. using a field format fluorescence detection instrument, such as Fluorimager™ from Molecular Dynamics. This type of fluorimeter is capable of determining fluorescence over a large area. It is also possible to detect fluorescence using a CCD camera and to transfer the image data to a computer. The image can be generated by illumination of the fluorophore with light of the wavelength that specifically excites it. Detection can be optimized by using a bandpass filter between the camera and the assay that is specific for the emission wavelength of the fluorophore.

Assays that measure a change in fluorescence are preferred as they are believed to result in the greatest sensitivity. Any method, however, can be used that measures a change in signal from one of the compounds involved in the reaction as a result of, for example, conversion of the substrate to product, or displacement of the labeled ligand from the target.

Assays for compounds that affect a chromogenic substrate, e.g., p-nitrophenylphosphate, is also useful. It is also possible, for example, to measure a change in absorbance. For example, NADP is a common cofactor in many enzymatic reactions. Absorbance changes as NADPH is converted to NADP by, for example, neutrophil NADPH oxidase (such as during an oxidative burst associated with an immune response). This change can be monitored to determine zones of inhibition for compounds that inhibit this and other enzymes that use NADP, NADPH, NAD, and NADH as co-factors. The sensitivity of assays that measure a change in absorbance is believed to be generally lower than those that measure a change in fluorescence.

Other examples of detectable changes resulting from conversion of substrate to product include chemiluminescent changes and scintillation changes. Scintillation changes can be detected as described above for receptor binding with the exception that a substrate is attached to the scintillant (i.e., to the bead or plate containing scintillant). For example, a radioactive reagent, such as tritiated farnesyl pyrophosphate, can be added to the substrate by an enzyme such as farnesyl protein transferase. Transferase inhibitors prevent addition of the tritiated farnesyl pyrophosphate to the substrate, resulting in a reduction in detectable scintillations; i.e., transferase inhibitors are found in zones of reduced scintillation. In an alternative assay, removal of the radioactive portion of a substrate attached to the scintillant, such as by cleaving with a protease, releases the radiolabeled portion (i.e., moves it away from the scintillant). In such an assay, protease inhibitors cause an increase in scintillation, i.e., are found in zones of increased scintillation. As noted above, the scintillation signal can be detected using x-ray film, or film that is specifically designed to detect tritium dependent scintillations.

For assaying binding to a target molecule, a labeled ligand provides a signal that indicates such binding. The label is preferably a fluorescent moiety that alters its signal as a result of target molecule binding. Examples of such fluorescent moieties are NBD and 5-(dimethylamino)-1-naphthalenesulfonyl (Dansyl) chloride.

Colloidal matrices that are useful for the lawn assay include silica gel, agar, agarose, pectin, polyacrylamide, gelatin, starch, gellan gum, cross-linked dextrans (such as Sephadex™) and any other matrix, including the particulate material of the present invention that allows diffusion of compound from the multilayered particles in a limited region. Low melting-temperature agarose is preferred, generally in an amount of 0.5–2.0%, wt./vol. The colloidal matrix can be chosen to obtain a desired rate of diffusion. It is generally preferred to use a matrix that allows a high concentration of compounds to be easily obtained.

In carrying out the assay to determine compounds that, for example, affect enzyme activity, the multilayered particles are preferably embedded in a matrix containing the relevant enzyme. Following cleavage, compound diffuses from the particle into the matrix and contacts the enzyme. Substrate is then added and, as it diffuses into the colloidal matrix, active compounds inhibit conversion to product. By following such a procedure, compounds to be screened are allowed to interact with enzyme before the enzyme contacts substrate. This is believed to be advantageous because it allows compounds the best opportunity to inhibit the enzyme, and thus results in the clearest zone of inhibition.

It is also possible to embed the multilayered particles in a matrix that contains dispersed substrate. Following cleavage, the matrix can be contacted with enzyme. This procedure is not believed to be as sensitive since the compounds may not efficiently bind to the enzyme.

Multilayered particles can also be applied to the matrix's surface and the compounds allowed to diffuse into the matrix. This can be done, for example, by arraying the multilayered particles on the surface of a stretched sheet of plastic film (e.g., Parafilm™), and then applying the sheet to the surface of the matrix.

In assaying for compounds that affect enzyme activity, two colloidal matrices can be used. For example, one matrix can contain enzyme and particles and the other can contain substrate. Contacting the surfaces of the matrices with each other allows the substrate to come into contact with the enzyme. It is also possible to add a solution of substrate over the surface of a matrix containing enzyme and embedded particles. Adding solution is preferred when, e.g., the substrate interferes with detection. Solution containing the substrate can be removed prior to determining the zones of activity.

When using the lawn assay to screen for binding to a target molecule, there is generally no need for more than one matrix. A matrix contains the target molecule bound to the labeled ligand which emits a detectable signal indicating binding to the target molecule. Compounds from the multilayered particles are diffused into the matrix, preferably from embedded particles using photolysis. Alternatively, however, labeled ligand can be diffused into the matrix from a second matrix (or liquid layer) after release of the compounds in the matrix. This allows the compounds to contact the receptor before interaction with the labeled ligand, which can be advantageous.

Compounds can be cleaved from the multilayered particles either before or after the particles are contacted with the colloidal matrix. For example, multilayered particles can contain acid cleavable linkers, as further described below. These linkers can be cleaved in a gaseous acidic atmosphere before placing the particle on the matrix. The compounds, although cleaved, remain on the surface of the particles and diffuse into the matrix when the particles are placed on it. It is even possible to cleave the compounds prior to pouring low-melt liquid agarose over the multilayered particles. While some of the compounds will be washed away, sufficient compound can remain on the particle's surface to result in a recognizable zone of activity.

Where the compounds are cleaved after the beads are embedded in the colloidal matrix, it is preferred to use photolysis, e.g., cleaving by exposure to UV light. By adjusting light exposure, it is possible to control the amount of compound that diffuses into the matrix. If more light is applied, by increasing intensity or duration, more cleavage results, in turn releasing more compound into the matrix. This allows the amount of active compound released to be adjusted, so that zones of activity are only produced for compounds that are most active. The amount of compound released can also be optimized to produce zones that are most distinct.

The multilayered particles can be in a random arrangement, or in an ordered one. Preparing a random arrangement of multilayered particles requires little effort. For example, a library of beads can be suspended in a solvent, such as ethanol, and deposited on the bottom of a Petri plate. After the solvent has completely evaporated, a layer of agarose containing the relevant enzyme or target molecule can be poured over the beads. Alternatively, an ordered array can be used to space beads apart and allow easier identification of those that are active. In one example of an ordered array, beads are arrayed on a rigid template, such as a thin glass disk having tapered holes. The tapered holes are sized to allow only single beads to settle into them. Beads are suspended in a solvent, such as ethanol, and washed over the top of the template to fill each hole with one bead. The beads can then be cleaved in the dry state, and the template set down on the colloidal matrix. Capillary action wets the beads, facilitating diffusion of the cleaved compounds into the matrix. Zones of activity can be observed immediately below beads containing active compounds. It is possible to remove the template prior to detecting zones of activity if an image of the template on the matrix is made. This image can later be used to correlate the zones of inhibition in the matrix with the positions of beads on the template.

Ordered arrays are also useful in identifying the compounds on particles that are associated with zones of activity. Specifically, the array can be ordered so that the position of the multilayered particle on the array corresponds to the identity of the compound. Thus, once an assay has been carried out, and the position on the array determined for a particle carrying an active compound, the identity of that compound can be easily determined.

The assay is preferably carried out so that there is slow diffusion of the compound from the multilayered particle following cleavage. This results in a high concentration of compound in the vicinity of the bead. Thus very little compound is required to cause a distinct zone of activity. Most of the compound remains on the particle for any subsequent assays that are required. Such further assays may be needed if more than one multilayered particle is found in the zone of activity. It may then be necessary to retest the particles from the zone to determine which releases the active compound. Reassaying may be required as a matter of course if many thousands of beads are screened at high density. Reassaying may also be desirable to test for selectivity, i.e. to determine which active compounds are inactive in a second assay that tests for a different property.

With combinatorial libraries containing thousands of related compounds, many compounds may be found that have some degree of activity. It therefore can be useful to use the lawn assay to distinguish the most potent compounds. In the assay, if the amount of compound released from each particle is approximately the same, potent compounds have a detectable effect further from the bead than weak compounds do, at any given time. Thus, the more active compounds create a larger zone of activity. Furthermore, the zone of activity of the most active compounds lasts longer. Thus, it is possible to quantitate the activity of the compound eluted from the multilayered particle by the size of the zone of activity, as well as by the duration of the zone following cleavage.

Reducing photolysis time reduces the amount of compound released from the particle. As the concentration of the compounds is lowered, those that are less active become more difficult to detect. As a result, the number of active compounds drops. In general it is found that compounds that are detectable at the shortest elution times, i.e., that are most potent, are also identified as most potent using conventional solution-phase screening. The activity of the inhibitors is found to correlate with the size and duration of the zone of activity: the most potent compounds produce the largest zones for the longest time, for any given amount of photolysis.

When assaying a library containing many active compounds, it may be desirable to screen using a low density of multilayered particles, i.e., a low number of particles per cm$^3$ of matrix. While requiring more assays to screen the entire library, it is less likely that particles will have to be retested to determine which contains the active compound. Screening a large library containing many active members at a low density is often more efficient than screening at high density, since rescreening particles is time consuming. The optimum density for screening can be determined for a given library by comparing the throughput in the initial assay with the effort required to re test active particles. Other factors which affect optimum screening density include the cost of the target and the size of the library.

It is also possible to test for compounds that, for example, interfere with proteins that inhibit enzyme activity using an electrophoretic assay. In such an assay, the most active compounds prevent enzyme inhibition, resulting in more enzymatic catalysis. Thus, when a fluorogenic substrate is used, active compounds result in a brighter zone of activity. For example, P16 is a known protein inhibitor of cyclin-dependent kinase-4 (Cdk-4). Using the lawn assay, Cdk-4, Cyclin D1, P16, a fluorogenic substrate and a library of beads to be screened can be included in a layer of low-melt agarose. Following photocleavage, and after allowing sufficient time to convert substrate to product, the gel can be subjected to an electrophoretic separation. Product migrates to the anode, where it is preferably trapped on an anode filter. The location of product on the filter indicates the position in the gel of compound that disrupts P16 inhibition of Cdk4.

In another embodiment of the lawn assay, an electrophoretic procedure is used to separate substrate from product to increase the sensitivity of the assay. In this embodiment, a substrate is used which changes charge when converted to product. An example of such a substrate is the peptide leu-arg-arg-ala-ser-leu-gly attached to a fluorophore, sold commercially as Pep-Tag™ (Promega Corp.). Protein kinase A (PKA) phosphorylates this substrate, which has net +1 charge, to form a phosphopeptide which has a net –1 charge. A lawn assay is performed in which PKA is contacted in a colloidal matrix with substrate and a library of potential inhibitors. An electrophoretic separation is then carried out across the width of (i.e., perpendicular to) the matrix. The phosphopeptide (i.e., product) moves towards the anode, and the dephosphopeptide (i.e., substrate) moves towards the cathode. If a membrane is applied to one or both sides of the matrix during electrotransfer, electroblotting can be achieved. For example, the phosphopeptide can be electroblotted to a suitable membrane, such as an Immobilon™ CD membrane. Alternately, the dephosphopeptide can be electrotransferred to an appropriate paper, such as Whatman™ 3 MM paper.

In another embodiment, the substrate and product can be chosen so that one is neutral and one is charged. Application of the electrophoretic field will remove the charged moiety. The resulting matrix will contain only the neutral moiety, thereby allowing detection of compounds that affect the conversion to product. The position of the bead containing the active compound can be determined by fluorescent imaging of the substrate or product, using, e.g., photography or video imaging. This technique increases sensitivity of the lawn assay by separating fluorescent substrate from fluorescent product, concentrating the fluorescent image, and by eliminating compounds from the matrix that might cause background signal. Other protein kinases and phosphatases such as protein kinase C, cyclin dependent kinases, MAP kinases, and inositol monophosphatase can also be used with appropriate substrates in this method. A protease can also be screened by this method by using a substrate consisting of an appropriate peptide linked to a labeling moiety, such as a fluorophore. The peptide sequence is chosen so that the substrate and product will migrate differentially in an electric field.

Enzymes that can be used in the assay include, but are not limited to, the following: Acid Phosphatase, Activated Protein C, Alkaline Phosphatase, Aminopeptidases B & M, Amyloid A4-Generating Enzyme, Angiotensinase, Aryl Sulfatase, beta -Galactosidase, beta -Glucosidase, beta -Glucuronidase, Calpains I & II, Cathepsins B, C, D, & G, Cholinesterase, Chymotrypsin, Collagenase, Dipeptidyl Peptidases I–IV, Elastase, Endothelin Converting Enzyme, Factor Xa, Factor Xla, Factor Xlla Df-Protease, Furin, gamma -Glutamyltranspeptidase, Granzymes A & B, HIV Protease, IL-1B Convertase, Kallikrein, Lysozyme, Mast Cell Protease, Peroxidase, Plasmin, Prohormone Convertase, GAMMA ANP Precursor Processing Enzyme, Renin, Spleen Fibrinolytic Proteinase, Staphylocoagulase, Thrombin, Tissue Plasminogen Activator, Trypsin, Tryptase and Urokinase. Other useful assays and methods of performing Lawn assays will be apparent to those of skill in the art.

G.8 Microarrays

In another preferred embodiment, the present invention provides a microarray comprising n compounds distributed over n regions of a substrate comprising a multilayered material of the invention.

In a preferred embodiment, each of the n compounds will be a different compound. In a still further preferred embodiment, the n compounds will be patterned on the substrate in a manner that allows the identity of each of the n locations to be ascertained. The microarray can be patterned from essentially any type of molecule, including small organic molecules, peptides, nucleic acids, carbohydrates, antibodies, enzymes, and the like.

In a preferred embodiment, n is a number from 2 to 100, more preferably, from 10 to 1,000, and more preferably from 100 to 10,000.

In yet another preferred embodiment, the invention also provides a method for preparing a microarray of n compounds comprising, attaching n compounds to n regions of a substrate comprising a multilayered material of the invention.

A variety of methods are currently available for making arrays of biological macromolecules, such as arrays of antibodies, nucleic acid molecules or proteins. The following discussion utilizes a DNA microarray as an exemplary microassay. This use of DNA is intended to be illustrative and not limiting. Microassays can be made with a wide range of other compound types.

One method for making ordered arrays of DNA on a porous membrane is a "dot blot" approach. In this method, a vacuum manifold transfers a plurality, e.g., 96, aqueous samples of DNA from 3 millimeter diameter wells to a porous membrane. A common variant of this procedure is a "slot-blot" method in which the wells have highly-elongated oval shapes.

The DNA is immobilized on the porous membrane by baking the membrane or exposing it to UV radiation. This is a manual procedure practical for making one array at a time and usually limited to 96 samples per array. "Dot-blot" procedures are therefore inadequate for applications in which many thousand samples must be determined.

A more efficient technique employed for making ordered arrays of genomic fragments uses an array of pins dipped into the wells, e.g., the 96 wells of a microtitre plate, for transferring an array of samples to a substrate, such as a porous membrane. One array includes pins that are designed to spot a membrane in a staggered fashion, for creating an array of 9216 spots in a 22×22 cm area. See, Lehrach, et al., HYBRIDIZATION FINGERPRINTING IN GENOME MAPPING AND SEQUENCING, GENOME ANALYSIS, Vol. 1, Davies et al, Eds., Cold Springs Harbor Press, pp. 39–81 (1990). A limitation with this approach is that the volume of DNA spotted in each pixel of each array is highly variable. In addition, the number of arrays that can be made with each dipping is usually quite small.

An alternate method of creating ordered arrays of nucleic acid sequences is described by Pirrung et al. (U.S. Pat. No. 5,143,854, issued 1992), and also by Fodor et al., (*Science*, 251: 767–773 (1991)). The method involves synthesizing different nucleic acid sequences at different discrete regions of a particle. This method employs elaborate synthetic schemes, and is generally limited to relatively short nucleic acid sample, e.g., less than 20 bases. A related method has been described by Southern et al. (*Genomics*, 13: 1008–1017 (1992)).

Khrapko, et al., *DNA Sequence,* 1: 375–388 (1991) describes a method of making an oligonucleotide matrix by spotting DNA onto a thin layer of polyacrylamide. The spotting is done manually with a micropipette.

None of the methods or devices described in the prior art are designed for mass fabrication of microarrays characterized by (i) a large number of micro-sized assay regions separated by a distance of 50–200 microns or less, and (ii) a well-defined amount, typically in the picomole range, of analyte associated with each region of the array. A substrate comprised of the particulate material of the invention is capable of meeting such requirements. The layout of a substrate using the particulate material of the invention, can be controlled by varying the size of the particles and their proximity to one another.

The substrate can also be patterned using techniques such as photolithography (Kleinfield et al., *J. Neurosci.* 8:4098–120 (1998)), photoetching, chemical etching and microcontact printing (Kumar et al., *Langmuir* 10:1498–511 (1994)). Other techniques for forming patterns on a substrate will be readily apparent to those of skill in the art.

The size and complexity of the pattern on the substrate is limited only by the resolution of the technique utilized and the purpose for which the pattern is intended. For example, using microcontact printing, features as small as 200 nm have been layered onto a substrate. See, Xia, Y.; Whitesides, G., *J. Am. Chem. Soc.* 117:3274–75 (1995). Similarly, using photolithography, patterns with features as small as 1 μm have been produced. See, Hickman et al., *J. Vac. Sci. Technol.* 12:607–16 (1994). Patterns which are useful in the present invention include those which comprise features such as wells, enclosures, partitions, recesses, inlets, outlets, channels, troughs, diffraction gratings and the like.

In a presently preferred embodiment, the patterning is used to produce a substrate having a plurality of adjacent wells, indentations or holes to contain the particles and wherein each of these features is isolated from the other wells by a raised wall or partition and the wells do not fluidically communicate. Thus, a particle, or other substance, placed in a particular well remains substantially confined to that well. In another preferred embodiment, the patterning allows the creation of channels through the device whereby an analyte or other substance can enter and/or exit the device.

The pattern can be printed directly onto the substrate or, alternatively, a "lift off" technique can be utilized. In the lift off technique, a patterned resist is laid onto the substrate, an organic layer is laid down in those areas not covered by the resist and the resist is subsequently removed. Resists appropriate for use with the substrates of the present invention are known to those of skill in the art. See, for example, Kleinfield et al., *J. Neurosci.* 8:4098–120 (1998). Following removal of the photoresist, a second organic layer, having a structure different from the first organic layer can be bonded to the substrate on those areas initially covered by the resist. Using this technique, substrates with patterns having regions of different chemical characteristics can be produced. Thus, for example, a pattern having an array of adjacent wells can be created by varying the hydrophobicity/hydrophilicity, charge and other chemical characteristics of the pattern constituents. In one embodiment, hydrophilic compounds can be confined to individual wells by patterning walls using hydrophobic materials. Similarly, positively or negatively charged compounds can be confined to wells having walls made of compounds with charges similar to those of the confined compounds. Similar substrate configurations are accessible through microprinting a layer with the desired characteristics directly onto the substrate. See, Mrkish, M.; Whitesides, G. M., *Ann. Rev. Biophys. Biomol. Struct.* 25:55–78 (1996).

G.9 Analytes

The materials, devices, and methods of the present invention can be used to detect any analyte, or class of analytes, which interact with a recognition moiety in a manner that perturbs the mesogenic layer in a detectable manner. The interaction between the analyte and recognition moiety can be any physicochemical interaction, including covalent bonding, ionic bonding, hydrogen bonding, van der Waals interactions, repulsive electronic interactions, attractive electronic interactions and hydrophobic/hydrophilic interactions.

In a preferred embodiment, the interaction is an ionic interaction. In this embodiment, an acid, base, metal ion or metal ion-binding ligand is the analyte. In a still further preferred embodiment, the interaction is a hydrogen bonding interaction. In a particularly preferred embodiment, the hybridization of an immobilized nucleic acid to a nucleic acid having a complementary sequence is detected. In another preferred embodiment, the interaction is between an enzyme or receptor and a small molecule which binds thereto.

In another embodiment, the analyte competes for the recognition moiety with another agent which has been bound to the recognition moiety prior to introducing the analyte of interest. In this embodiment, it is the process or result of the analyte displacing the pre-bound agent which causes the detectable perturbation in the mesogenic layer. Suitable combinations of recognition moieties and analytes will be apparent to those of skill in the art.

In presently preferred embodiments, the analyte is a member selected from the group consisting of acids, bases, organic ions, inorganic ions, pharmaceuticals, herbicides, pesticides, chemical warfare agents, noxious gases and biomolecules. Importantly, each of these agents can be detected as a vapor or a liquid. These agents can be present as components in mixtures of structurally unrelated compounds, racemic mixtures of stereoisomers, non-racemic mixtures of stereoisomers, mixtures of diastereomers, mixtures of positional isomers or as pure compounds. Within the scope of the invention is a device and a method to detect a particular analyte of interest without interference from other substances within a mixture.

Both organic and inorganic acids can be detected using the device and method of the present invention. In a preferred embodiment, the recognition moiety comprises a group which is protonated by the acid.

In another preferred embodiment, the invention provides a device and a method for detecting bases. The methods for the detection and the mechanisms which allow such detection of bases are substantially similar to those discussed above in the context of acid detection; the notable exception being that the base will preferably deprotonate a group on a SAM component, spacer arm or metal film.

Organic ions which are substantially non-acidic and non-basic (e.g., quaternary alkylammonium salts) can be detected by a recognition moiety. For example, a recognition moiety with ion exchange properties is useful in the present invention. A specific example is the exchange of a cation such as dodecyltrimethylammonium cation for a metal ion such as sodium. Recognition moieties that form inclusion complexes with organic ions are also of use. For example, crown ethers and cryptands can be used to form inclusion complexes with organic ions such as quaternary ammonium cations.

Inorganic ions such as metal ions and complex ions (e.g., $SO_4^{-2}$, $PO_4^{-3}$) can also be detected using the device and method of the invention. Metal ions can be detected, for example, by their complexation or chelation by agents bound to a SAM component, spacer arm or the substrate. In this embodiment, the recognition moiety can be a simple monovalent moiety (e.g., carboxylate, amine, thiol) or can be a more structurally complex agent (e.g., ethyienediamine-pentaacetic acid, crown ethers, aza crowns, thia crowns).

Complex inorganic ions can be detected by their ability to compete with ligands for bound metal ions in ligand-metal complexes. When a ligand bound to a SAM component, a spacer arm or a substrate forms a metal-complex having a thermodynamic stability constant which is less than that of the complex between the metal and the complexion, the complex ion will cause the dissociation of the metal ion from the immobilized ligand. The dissociation of the metal ion will perturb the mesogenic layer in a detectable manner. Methods of determining stability constants for compounds formed between metal ions and ligands are well known to those of skill in the art. Using these stability constants, devices which are specific for particular ions can be manufactured. See, Martell, A. E., Motekaitis, R. J., DETERMINATION AND USE OF STABILITY CONSTANTS, 2d Ed., VCH Publishers, New York 1992.

Small molecules such as pesticides, herbicides, agents of war, and the like can be detected by the use of a number of different recognition moiety motifs. Acidic or basic components can be detected as described above. An agent's metal binding capability can also be used to advantage, as described above for complex ions. Additionally, if these agents bind to an identified biological structure (e.g., a receptor), the receptor can be immobilized on the substrate, a SAM component or a spacer arm. Techniques are also available in the art for raising antibodies which are highly specific for a particular small molecule. Thus, it is within the scope of the present invention to make use of antibodies against small molecules for detection of those molecules.

In a preferred embodiment, the affinity of an analyte for a particular metal ion is exploited by having a SAM component, spacer arm or substrate labeled with an immobilized metal ion. The metal ion generally must have available at least one empty coordination site to which the analyte can bind. Alternatively, at least one bond between the metal and the metal-immobilizing agent must be sufficiently labile in the presence of the analyte to allow the displacement of at least one bond of the immobilizing reagent by the analyte.

In a preferred embodiment, the agent detected by binding to an immobilized metal ion is an organophosphorous compound such as an insecticide or an agent of war (e.g., VX, O-ethyl-S-(2-diisopropylaminoethyl)-methylthiophosphonate). Exemplary compounds which exhibit affinity for organophosphorous agents include, but are not limited to, $Cu^{+2}$-diamine, triethylentetraamine-$Cu^+$ 2-chloride, tetraethylenediamine-$Cu^{+2}$-chloride and 2,2'-bipyridine-$Cu^{+2}$-chloride. See, U.S. Pat. No. 4,549,427, issued to Kolesar, Jr., E. S. on Oct. 29, 1985.

In another preferred embodiment, antibodies to the particular agents are immobilized on the substrate, a SAM component or a spacer arm. Techniques for raising antibodies to herbicides, pesticides and agents of war are known to those of skill in the art. See, Harlow, Lane, MONOCLONAL ANTIBODIES: A LABORATORY MANUAL, Cold Springs Harbor Laboratory, Long Island, N.Y., 1988.

In a preferred embodiment, the herbicides are preferably members of the group consisting of triazines, haloacetanilides, carbamates, toluidines, ureas, plant growth hormones and diphenyl ethers. Included within these broad generic groupings are commercially available herbicides such as phenoxyl alkanoic acids, bipyridiniums, benzonitriles, dinitroanilines, acid amides, carbamates, thiocarbamates, heterocyclic nitrogen compounds including triazines, pyridines, pyridazinones, sulfonylureas, imidazoles, substituted ureas, halogenated aliphatic carboxylic acids, inorganics, organometallics and derivatives of biologically important amino acids.

In the embodiments discussed above, the preferred agent of war is a member of the group consisting of mustard and related vesicants including the agents known as HD, Q, T, HN1, HN2, HN3, nerve agents, particularly the organic esters of substituted phosphoric acid including tabun, sarin, isopropyl methylphosphonofluoridate, soman pinacolyl methylphosphonofluoridate. Other detectable analytes include incapacitants such as BZ, 3-quinuclidinyl benzilate and irritants such as the riot control compound CS.

Pesticides preferred for detection using the present invention include bactericides (e.g., formaldehyde), fumigants (e.g., bromomethane), fungicides (e.g., 2-phenylphenol, biphenyl, mercuric oxide, imazalil), acaricides (e.g., abamectin, bifenthrin), insecticides (e.g., imidacloprid, prallethrin, cyphenothrin)

The present invention also provides a device and a method for detecting noxious gases such as CO, $CO_2$, $SO_3$, $H_2SO_4$, $SO_2$, NO, $NO_2$, $N_2O_4$ and the like. In a preferred embodiment, the SAM, the substrate or a spacer arm includes at least one compound capable of detecting the gas. Useful compounds include, but are not limited to, palladium compounds selected from the group consisting of palladium sulfate, palladium sulfite, palladium pyrosulfite, palladium chloride, palladium bromide, palladium iodide, palladium perchlorate, palladium complexes with organic complexing reagents and mixtures thereof.

Other compounds of use in practicing this embodiment of the present invention include, molybdenum compounds such as silicomolybdic acid, salts of silicomolybdic acid, molybdenum trioxide, heteropolyacids of molybdenum containing vanadium, copper or tungsten, ammonium molybdate, alkali metal or alkaline earth salts of molybdate anion, heteropolymolybdates and mixtures thereof.

Still further useful gas detecting compounds include, copper salts and copper complexes with an available coordination site. Alpha-cyclodextrin, beta-cyclodextrin, modified alpha- and beta-cyclodextrins, gamma-cyclodextrin and mixtures thereof are of use in practicing the present invention. See, U.S. Pat. No. 5,618,493, issued to Goldstein et al. on Apr. 8, 1997 and No. 5,071,526, issued to Pletcher et al. on Dec. 10, 1991.

In another preferred gas detecting embodiment, the substrate, SAM component or spacer arm is derivatized with a compound selected from the group consisting of amorphous hemoglobin, crystalline hemoglobin, amorphous heme, crystalline heme and mixtures thereof. The heme serves as a recognition moiety which is reactive towards the gas. See, U.S. Pat. No. 3,693,327, issued to Scheinberg, I. A. on Sep. 26, 1972.

When the analyte is a biomolecule, any recognition moiety which interacts with the biomolecule is useful in practicing the present invention. Thus, when the analyte is a nucleic acid, in one embodiment, the recognition moiety is a nucleic acid having a sequence which is at least partially complementary to the recognition moiety sequence. When the recognition moiety is a peptide, an antibody specific for that peptide can be used as the analyte. In another preferred embodiment, a protein, other than an antibody (e.g., enzyme, receptor) is the analyte.

Other combinations of analytes and recognition moities will be apparent to those of skill in the art.

H. Compositions, Kits and Integrated Systems

The invention provides compositions, kits and integrated systems for practicing the various aspects and embodiments of the present invention, including producing the particulate materials, performing the chromatographic separations, performing the syntheses and practicing the assays.

The invention provides kits for practicing the methods noted above. The kits can include any of the compositions noted above, and optionally further include additional components such as instructions to practice the methods, one or more containers or compartments (e.g., to hold the particulate material, nucleic acids, antibodies, inhibitors or the like), a robotic armature for mixing kit components, printing microarrays or the like.

The invention also provides integrated systems for performing the methods disclosed herein. For example, in the assembly of microarrays, combinatorial libraries or performing assays, in one embodiment, the delivery of individual compounds or compound components is accomplished by means of a robotic armature which transfers fluid from a source to a destination, a controller which controls the robotic armature, a label detector, a data storage unit which records label detection, and an assay component such as a microtiter dish comprising a well having the multilayered particulate material or a substrate comprising a fixed multilayered particulate material. When a labeled compound is used, it is detected by means of the label detector.

A number of robotic fluid transfer systems are available, or can easily be made from existing components. For example, a Zymate XP (Zymark Corporation; Hopkinton, Mass.) automated robot using a Microlab 2200 (Hamilton; Reno, N.V.) pipetting station can be used to transfer parallel samples to 96 well microtiter plates to set up several parallel simultaneous ligation reactions.

Optical images viewed (and, optionally, recorded) by a camera or other recording device (e.g., a photodiode and data storage device) are optionally further processed in any of the embodiments herein, e.g., by digitizing the image and storing and analyzing the image on a computer. A variety of commercially available peripheral equipment and software is available for digitizing, storing and analyzing a digitized video or digitized optical image, e.g., using PC (Intel x86 or Pentium chip-compatible DOS™, OS2™ WINDOWS™, WINDOWS NT™ or WINDOWS95™ based machines), MACINTOSH™, or UNIX based (e.g., SUN™ work station) computers.

One conventional system carries light from the specimen field to a cooled charge-coupled device (CCD) camera, in common use in the art. A CCD camera includes an array of picture elements (pixels). The light from the specimen is imaged on the CCD. Particular pixels corresponding to regions of the specimen (e.g., individual hybridization sites on an array of multilayered particles) are sampled to obtain light intensity readings for each position. Multiple pixels are processed in parallel to increase speed. The apparatus and methods of the invention are easily used for viewing any sample, e.g., by fluorescent or dark field microscopic techniques.

The materials, methods and devices of the present invention are further illustrated by the examples which follow. These examples are offered to illustrate, but not to limit the claimed invention.

EXAMPLES

In Example 1, the deposition of electroless gold on a silica particle is demonstrated. The surface is characterized using X-ray diffraction and electron microscopy.

Example 2 describes the synthesis of the components of representative organic layers and their adsorption onto a gold surface.

Example 3 describes a study undertaken to determine the extent of irreversible adsorption of the enzyme subtilisin BPNI onto bare silica gel, silica gel supporting electroless gold, and silica gel supporting electroless gold that was treated by immersion in ethanoic solutions of ω-substituted alkanethiols.

In Example 4, particles of the invention having biotinylated SAMs were prepared and utilized to study the binding of an affinity ligand (streptavidin) to an immobilized "recognition moiety" (biotin). The binding of streptavidin and the SAM bound-biotin was demonstrated.

In Example 5, a series of experiments was performed to demonstrate that SAMs supported on gold-coated silica gel form a useful system with which to measure the activity of enzymes at surfaces.

Example 1

Example 1 illustrates the procedure utilized to deposit electroless gold onto a silica substrate.

1.1 Materials

Electroless gold was prepared from an aqueous solution of $Na_3Au(SO_3)_2$ purchased from Technic, Inc. Silica gel (50–200 mesh, particle sizes ranging from 50 to 200 μm, surface area of 300–500 m$^2$/g, pore volume between 0.75 cm$^3$/g and 1.2 cm$^3$/g, and pore diameters between 60 Å and 150 Å) was purchased from Aldrich.

1.2 Deposition of Electroless Gold

The experimental procedure used to coat the silica gel with gold was adapted from methods reported in the past for electroless deposition of gold onto polymeric membranes for filtration (Menon, V.P. et al., *Anal Chem* 67:1920 (1995)). A sample of silica gel was treated with "piranha solution" (70% $H_2SO_4$, 30% $H_2O_2$; Caution: "piranha solution" reacts violently with organic materials), rinsed with water and dried. A "sensitizer" ($Sn^{2+}$) was adsorbed to the surface of the silica by immersion of the gel (with stirring) in a solution of 26 mM $SnCl_2$ and 70 mM trifluoroacetic acid using, 50/50 methanol/water as the solvent. The silica gel was immersed in this solution for 3 minutes and then rinsed with methanol. The $Sn^{2+}$ ions adhere to the pore walls and form a two-coordinate complex with silanol groups on the surface of silica (Menon, V. P. et al., *Anal Chem* 67:1920 (1995); Koura, N. *Electroless Plating of Silver, In: Electroless Plating: Fundamentals and Applications, Ed.;* Mallory, G. O. et al. *American Electroplaters and Surface Finishers Society, Orlando,* (1990)). The $Sn^{2+}$-primed silica gel was then activated by immersion in an aqueous solution of ammoniacal $AgNO_3$ (29 mM) for 2 min. This procedure leads to a redox reaction in which the surface bound $SN^{2+}$ is oxidized to $Sn^{4+}$ and $Ag^+$ is reduced to elemental Ag (on the surface of the silica). Following deposition of Ag, the silica gel was rinsed with methanol and water.

Silica gel treated with Ag was then immersed (with stirring) in an aqueous solution of 7.9 mM $Na_3Au(SO_3)_2$, 0.127 M $Na_2SO_3$ and 0.625 M formaldehyde for 60 min. The temperature of the bath was 4° C. The silver particles on the surface of the silica gel act as catalytic sites for oxidation of formaldehyde and concurrent reduction of $Au^+$ to elemental gold (Menon, V. P. et al., *Anal Chem* 67:1920 (1995).

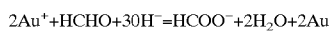

$2Au^+ + HCHO + 3OH^- = HCOO^- + 2H_2O + 2Au$

After the silica gel was coated with gold, it was rinsed thoroughly with water and immersed in 25% nitric acid for 12 hours. This step was performed to dissolve residual Ag and Sn particles exposed on the surface of the gel. The silica gel was then rinsed with water, methanol and dried. The dry product was dark red and had a crystalline appearance.

1.3 X-ray Diffractometry and Scanning Electron Microscopy

The diffraction of x-rays from gold deposited onto silica gel was measured using Cu Kα x-rays (wavelength, 1.5406 Å) and a Rigaku x-ray diffractometer operated in θ/2θ mode. A Ge (111) monochromator and a scintillation counter were used. Scanning electron microscopy was performed using an ISI DI-130 microscope. Images were collected by using electrons back-scattered from the samples.

1.4 Results

Scanning electron microscopy (SEM) and x-ray diffractometry (XRD) were used to characterize the electroless gold deposited onto the silica gel. Images (FIG. 1) of the gold-coated silica gel obtained by SEM show the surface of the gel to be smooth and featureless on scales of micrometers (except for a few cracks and dust particles). Images obtained from back-scattered electrons show the presence of a few 0.5–1.0 μm-sized metal aggregates on the surface of the 50–200 μm-sized gel particles.

By plating onto glass microscope slides, the thickness of the film of gold on the gel was estimated to be ~100 Å. Thus a large fraction of the pores of the silica (which are typically 60–15 Å in diameter) were expected to be filled with gold. X-ray diffraction patterns obtained from gold supported on the silica gel showed the gold to be polycrystalline with crystallographic orientations of (111), (200), (220) and (311). These results were consistent with the results of Hou and coworkers, who recently reported XRD patterns of electroless gold deposited on planar glass slides (Hou, Z. et al., *Langmuir* 14:3287 (1998)). No direct structural evidence for completeness of the coating of the silica by the gold was obtained. However, it was demonstrated that irreversible adsorption of subtilisin BPN$^{-1}$ onto bare silica gel is eliminated when the gel supports electroless gold derivatized by a SAM formed from $HO(CH_2CH_2O)_2(CH_2)_{11}$ SH.

As described in the Methods section, 500 mg of gold-coated silica gel was used in each experiment. The weight of gold on the surface of 500 mg of gold-coated gel silica gel is, therefore, unlikely to prevent the use of these supports for biological assays. In comparison, (solid) gold particles (diameter 2–8 μm) with a comparable surface area (~0.5 m$^2$) would weigh—4000 mg and cost—$140.

Example 2

Example 2 describes the synthesis of the components of representative organic layers and their adsorption onto the gold surface.

2.1 Materials and Methods

The monolayer component, (1-mercaptoundec-11-yl)di (ethylene glycol) was prepared using the procedures described by Prime & Whitesides (Prime, K. L. et al., *J. Am. Chem. Soc.* 115:10714 (1993). The 12-mercapto-(8'-biotinoylamido-3,6-dioxaoctyl)dodecylamide and biotin-(11-mercapto)undecylester were synthesized and purified as described by Haussling & Ringsdorf (Haussling, L. et al. *Angew. Chem. Int. Ed. Engl.* 30:569 (1991); Haussling, L.

et al. *Langmuir* 7:1837 (1991). The synthesis of suc-Ala-Ala-Pro-Phe-p-nitroanilide-(11-mercapto)undecylester (pNA-FPAA-suc-(CH$_2$)$_{11}$SH), HO(C$_2$)$_{11}$SH and HOOC(CH)$_{10}$SH are described in Dubrovsky et al. (submitted for publication to *Langmuir*). CH$_3$(CH$_2$)$_{11}$SH was purchased from Aldrich.

2.2 Formation of SAMs

SAMs were formed from pNA-FPAA-suc-(CH$_2$)$_{11}$SH on the surface of the gold-coated silica gel by immersing the gel into ethanolic solutions containing 10 mM thiol. The derivatized gel was subsequently washed with ethanol, water and Tris buffer before use. The gold-coated silica gel (500 mg) supporting the SAM was incubated in Tris buffer containing subtilisin BPN[1] (100 pmol/ml) for 6 hrs, and then immersed into a aqueous solution containing 200 mM NaOH to complete hydrolysis of the pNA. The concentration of pNA released from the surface of the gel after each step was determined by measurement of the absorbance of the solution at a wavelength of light of 410 nm ($\epsilon_{412}$=8480 M$^{-1}$ cm$^{-1}$). Coadsorption of pNA-FPAA-suc(CH$_2$)$_{11}$SH and X(CH$_2$)$_{11}$SH, where X=CH$_3$, COOH and OH, was used to form mixed monolayers. The composition of the mixed SAMs was determined by alkaline hydrolysis (200 mM NaOH) of pNA from the mixed SAM.

2.3 Results

FTIR spectra of self-assembled monolayers formed form 1-hexadecanethiol on electroless gold supported on glass microscope slides have been measured by Hou and coworkers (Hou, Z. et al., *Langmuir* 14:3287 (1998)). Vibrational bands corresponding to symmetric and asymmetric H-C-H stretching vibrations were found at 2850 cm$^{-1}$ and 2918 cm$^{-1}$, respectively, indicating that long-chain alkanethiols do form densely packed monolayers on electroless gold. Electrochemical methods of characterization as well as measurements of contact angles further support the conclusion that densely-packed SAMs can be formed on electroless gold prepared by using the procedure described above. For example, the fractional coverage of the surface of electroless gold by a SAM formed from 1-hexadecanethiol was estimated to be 99.98% by using cyclic voltammetry. Here we use the fact that densely-packed SAMs form on electroless gold to estimate the available surface area of electroless gold supported on silica gel.

Self-assembled monolayers were formed on gold-coated silica gel by suspending the gel in ethanol containing 1 of 1-dodecanethiol for 12 hours. The extent of adsorption of the alkanethiol from solution was measured by difference analysis using Ellman's test (Dubrovsky, T. et al., submittedfor publication to *Langmuir*). In the presence of free sulfhydryl groups, Ellman's reagent, 5,5'-dithiobis(2-nitrobenzoic acid), is reduced to 5-sulfido-2-nitrobenzoate (TNB). The intense yellow color of TNB was quantified by measuring its absorbance at 412 nm ($\epsilon_{412}$=13,600 M$^{-1}$ cm$^{-1}$). By using this method, the surface area of gold on the silica gel that adsorbed 1-dodecanethiol was found to be 0.93–1.28 m$^2$/g (assuming 25 Å$^2$/molecule within the SAM (Ulman, A. *An Introduction to Ultrathin Organic Films: From Langmuir-Blodgett to Self-Assembly*, Academic Press, Boston (1991)). The smaller specific surface area of the gold-coated silica gel as compared to bare silica gel (300–500 m$^2$/g) is consistent with our expectation that the gold plugs many of the pores of the gel. Although relatively small, we note that the specific surface area of the gold-coated gel is, in fact, sufficiently large to permit routine measurement of a change in bulk concentration of analyte released into solution from the surface of the gel (e.g., pNA). We also point out that gold-coated silica gel has a specific surface area that is higher than commercially available gold particles with diameters ranging between 2 and 8 μm (0.24 to 0.349 m$^2$/g by adsorption of 1-dodecanethiol).

Self-assembled monolayers formed from HO(CH$_2$)$_{11}$SH and HOOC(CH$_2$)$_{11}$SH lead to surface concentrations of carboxyl or hydroxyl group that range between 5–6 μmol/m$^2$. With large and bulky terminal groups, however, as with the tetrapeptide AAPF-pNA, such high densities of packing are not possible. By using base (200 mM NaOH) to hydrolyze pNA from SAMs formed from pNA-FPAA-suc-(CH$_2$) 11SH on the surface of electroless gold, the surface density of AAPF-pNA was determined to be 2.6 μmol/m$^2$. This areal density is consistent with the cross-sectional area of AAPF (~60 Å$^2$/molecule).

Example 3

Example 3 describes a study undertaken to determine the extent of irreversible adsorption of the enzyme subtilisin BPN[1] onto bare silica gel, silica gel supporting electroless gold, and silica gel supporting electroless gold that was treated by immersion in ethanoic solutions of ω-substituted alkanethiols.

3.1 Materials and Methods

Subtilisin BPN[1] was employed because, in companion experiments, this enzyme was used to demonstrate that SAMs supported on gold-coated silica gel can be used to optimize enzymatic reactions at surfaces. Affinity purified streptavidin (60 kD, pI 5.0) was obtained from Pierce. Wild-type subtilisin BPN[1] (BC 3.4.21.14) was a gift from the Miami Valley Laboratories, The Procter & Gamble Company (stock solution in 50:50 propylene glycol/10 mM MES buffer containing 10 mM of CaCl$_2$, pH 5.5). At the time of use, the stock solution of the enzyme was eluted through an Econo-Pac 10 DG (Bio-Gel P-6DG) size exclusion chromatography column (Bio-Rad Laboratories) so as to exchange the storage buffer for Tris buffer (100 mM, pH 8.6, 10 mM CaCl$_2$). All experiments were carried out in the Tris buffer. The extent of irreversible adsorption of the enzyme to the gel was measured by preparing mini-columns from 500 mg of the gel (stationary phase) and loading 32 nmol of the enzyme onto the columns in 3 ml of buffer. The total concentration of enzyme in the eluent stream was used to determine the extent of irreversible adsorption of the enzyme onto the stationary phase within the mini-column.

3.2 Results

The irreversible adsorption of subtilisin BPNI onto SAMs formed on gold-coated silica gel was investigated for two reasons. First, because subtilisin BPN[1], adsorbs irreversibly onto silica gel under the solution conditions used, the extent of irreversible adsorption of subtilisin BPN[1] onto SAMs supported on gold-coated silica gel was a useful index of the extent to which the gold and SAM block the surface of the silica gel. Second, elimination of irreversible, non-specific adsorption of proteins is often necessary when designing biological assays (e.g., immunological assays) (Wild, IMMUNOASSAY HANDBOOK Macmillan, New York, (1994)).

The extent of irreversible adsorption of subtilisin BPN[1] onto bare silica gel and modified silica gel was determined by measuring the absorbance of a solution of enzyme ($\epsilon$280=32200 M$^{-1}$ cm$^{-1}$) before and after passage through a column containing gel. The measurements were performed in Tris buffer at pH 8.6, which corresponds to the isoelectric point of subtilisin BPN[1] and a maximum in the hydrolytic activity of the enzyme. First, the column was contacted with 3 ml of Tris buffer containing 32 nmol of subtilisin BPN[1] for 40 minutes. Following this contact period, buffer was passed through the column until enzyme could not be detected in the eluent stream.

Table 1 shows the amount of enzyme irreversible adsorbed to untreated and modified silica gel. Whereas 14 nmol of subtilisin BPN[1] was irreversibly adsorbed to untreated silica gel, we observed no irreversible adsorption of the enzyme onto gel presenting di(ethylene glycol) groups. We note that gold-coated gel (not treated with a SAM) irreversibly adsorbed 8 nmol of subtilisin BPN[1], and thus the SAM is needed to prevent irreversible adsorption. Because the bare silica gel irreversibly adsorbed subtilisin BPN[1] whereas the gold coated silica gel supporting SAMs formed from $HO(CH_2CH_2O)_2(CH_2)_{11}SH$ did not, it was concluded that elecroless gold in combination with the SAMs can be used to block sites on the silica gel responsible for irreversible adsorption of subtilisin BPN[1]. The extent of irreversible adsorption of subtilisin BPN[1] to the SAMs presenting hydroxyl and methyl groups is also small. In these cases, however, the volume of buffer required to elute a specified fraction of the adsorbed protein was observed to be greater than for SAMs presenting di(ethylene glycol).

| Stationary Phase (500 mg) | Irreversibly Adsorbed Subtilisin BPN[1] (nmol) |
|---|---|
| silica gel (untreated) | 14 |
| electroless gold on silica gel | 8 |
| $CH_3(CH_2)_{11}S$ on electroless gold on silica gel | 2 |
| $HO(CH_2)_{11}S$ on electroless gold on silica gel | 1 |
| $HO(CH_2CH_2O)_2(CH_2)_{11}S$ on electroless gold on silica gel | 0 |

Example 4

Particles of the invention having biotinylated SAMs were prepared and utilized to study the binding of an affinity ligand (streptavidin) to an immobilized "recognition moiety" (biotin). The binding of streptavidin and the SAM bound-biotin was demonstrated.

4.1 Materials and Methods

SAMs were prepared from 12-mercapto-(8'-biotinoylamido-3,6-dioxaoctyl)dodecylamide and biotin-(1-mercapto)undecylester on the surface of gold-coated silica gel by immersion of the gel into 10 nM ethanolic solutions of these thiols for 12 hours. Binding of streptavidin to these SAMs was performed by incubation of the derivatized gel for 40 minutes in 100 mM phosphate buffer (pH 7.4) containing 0.5 µM of streptavidin, followed by rinsing of the gel with copious volumes of phosphate buffer and deionized water. The density of streptavidin adsorbed to the surface of the SAM was assayed by specific binding of biotin-p-nitrophenyl ester from 50 mM acetate buffer at pH. 5.0. The concentration of biotin-p-nitrophenyl ester bound to the streptavidin monolayer was determined spectrophotometrically by following the alkaline hydrolysis of p-nitrophenol at a wavelength of 412 nm ($\epsilon_{412}$=13800 $M^{-1}$ $cm^{-1}$).

4.2 Results

That gold-coated silica gel can support affinity ligands for specific binding of proteins was also demonstrated. First, biotinylated thiols (Haussling, L. et al. *Angew. Chem. Int. Ed. Engl.* 30:569 (1991); Haussling, L. et al. *Langmuir* 7:1837 (1991) were self-assembled from ethanolic solutions (10 mM) onto the surface of silica particles coated with electroless gold. These surfaces were subsequently immersed into 100 mM phosphate buffer pH 7.4 containing streptavidin for 40 minutes and then rinsed thoroughly. By binding biotin-p-nitrophenyl ester to the immobilized streptavidin (see Materials and Methods), the surface concentration of streptavidin was calculated to be 4–7 pmol/$cm^2$, assuming that two or three binding sites were available on each immobilized streptavidin molecule for binding of biotin-p-nitrophenyl ester. These values are consistent with the formation of a monolayer of protein in which the area per streptavidin molecule ranged between 4100 and 2400 $Å^2$. This result demonstrates that it is possible to use gold-coated silica gel to support a SAM bearing an affinity ligand that binds a protein. The binding of biotin-p-nitrophenyl ester to the streptavidin is, in addition, a simple demonstration of the use of this system to form sandwich (multilayer) structures at surfaces (biotinylated thiol/streptavidin/biotinylated nitrophenyl ester). Although the strong binding constant of streptavidin for biotin ($K_4=10^{-15}$ M) is not representative of the majority of protein-ligand interactions ($K_4=10^{-9}$–$10^{-6}$ M), the high affinity and specificity of the streptavidin-biotin interaction makes it a useful element of many immunoassays. Monolyers of streptavidin immobilized on the surface of gold-coated silica gel could be used, for instance, to orient biotinylated antibodies or its Fab fragments with their antigen binding sites directed away from the surface (Leckband, D. E. et al., *Biochemistry* 24:11467 (1995) or to immobilize biotinylated nucleic acid probes.

Example 5

A series of experiments was performed to demonstrate that SAMs supported on gold-coated silica gel form a useful system with which to measure the activity of enzymes at surfaces. This capability was demonstrated through the preparation of a series of mixed SAMs that hosted a substrate for subtilisin BPN[1] at differed areal densities and within different microenvironments. Both of these factors were found to influence the extent of hydrolysis of the substrate by subitilisin BPN[1]. Understanding the extent of hydrolysis of surface-immobilized substrates by proteases such as subtilisin BPN[1] is important because substrates of these enzymes are often sequestered at interfaces when these enzymes are used in biotechnology (e.g., in detergents).

5.1 Materials and Methods

Mixed SAMs were formed for pNA-FPAA-suc-($CH_2$)$_{11}$SH and X($CH_2$)$_{11}$SH, where X=CH3, OH and COOH, on the surface of silica gel coated with electroless gold by coadsorption of thiols (10 mM total thiol concentration) from ethanolic solutions. Surface concentrations of the immobilized tetrapeptide were determined by alkaline hydrolysis of p-nitroanilide.

5.2 Results

Figure 2:
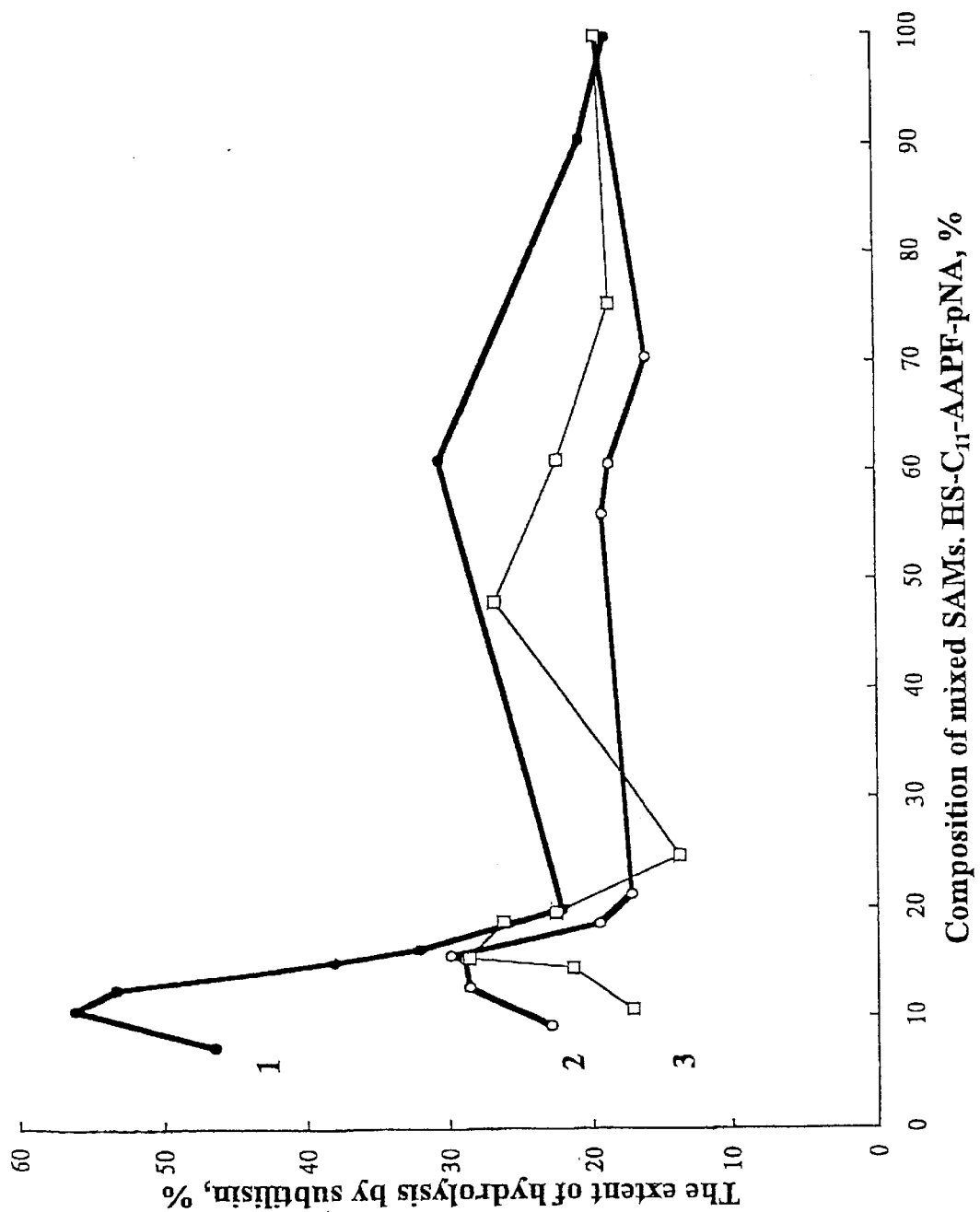
FIG. 2 is a plot of the extent of enzymatic hydrolysis of pNA vs. composition for mixed SAMs formed by coadsorption of pNA-FPAA-suc-$(CH2)_{11}SH$ and $CH_3(CH_2)_{11}SH(1)$, $HO(CH_2)_{11}SH(2)$ or $HOOC(CH_2)_{11}SH$.

The main results are shown in FIG. 2 and can be summarized as follows. First, the extent of enzymatic hydrolysis of pNA was measured to be ≈22% for SAMs formed from pNA-FPAA-suc-($CH_2$)$_{11}$SH (single-component SAM). That is, 78% of the substrate was inaccessible to the enzyme. A similar result was obtained by using micrometer-sized particles of solid gold (not gold formed by electroless deposition on silica gel) (Dubrovsky, T. et al., submitted for publication to *Langmuir*). Second, when the substrate was diluted by coadsorption with HO(CH$_2$)$_{11}$SH, the maximal extent of hydrolysis of the substrate in the mixed SAM increased to 30%. Third, when a mixed SAM was formed by coadsorption of pNA-PFAAsuc-(CH$_2$)11SH and CH$_3$(CH$_2$)$_{11}$SH such that the mole fraction of the hydrophobic component in the SAM was 0.9, the extent of hydrolysis increased to 55%. In short, the experimental measurements using SAMs on gold-coated silica gel demonstrate that dilution of the substrate into a hydrophobic environment (mixed SAM formed for pNA-FPAA-suc-(CH$_2$)$_{11}$SH and 1-dodecanethiol) maximizes the extent of hdyrolysis of AAPF-pNA by subtilisin BPN$^1$. The extent of hydrolysis of the substrate within the mixed hydrophobic SAM was greater by a factor of 2.5 as compared to the SAM formed from only pNA-PFAAsuc-(CH$_2$)$_{11}$SH. These results demonstrate that SAMs formed on gold-coated silica gel can be used to create interfacial environments for optimizing enzymatic reactions.

One or more of a variety of factors may be responsible for the variations in the extent of hydrolysis of pNA that reported in FIG. 2. For example, the orientations of the tetrapeptide moiety of the substrate molecule is a SAM, or the mobility and orientation of the enzyme on the SAM, will likely change with the compositions of the mixed SAMs. Reflection-absorption, Fourier-transformed infrared (RA-FTIR) spectra obtained using SAMs formed from pNA-FPAA-suc-(CH$_2$)$_{11}$SH on the surface of evaporated films of gold imply that the conformation of the tetrapeptide within the SAM is such that the aromatic rings of Phe arc constrained to be parallel to the surface, (Dubrovsky, T. et al., submittedfor publication to *Langmuir*). Whether or not the orientation of the Phe group is constrained in the mixed SAMs on electroless gold is unknown.

It is understood that the examples and embodiments described herein are for illustrative purposes only and that various modifications or changes in light thereof will be suggested to persons skilled in the art and are to included within the spirit and purview of this application and are considered within the scope of the appended claims. All publications, patents, and patent applications cited herein are hereby incorporated by reference in their entirety for all purposes.

What is claimed is:

1. A multilayered material comprising:
   a particulate substrate;
   a metal film essentially completely coating said substrate and layered onto said substrate by electroless deposition;
   an organic layer attached to said metal film; and
   a recognition moiety covalently attached to said organic layer.

2. The material according to claim 1, wherein said substrate is a member selected fro the group consisting of silicon oxides and aluminum oxides.

3. The material according to claim 1, wherein said substrate is silicon dioxide.

4. The material according to claim 1, wherein said substrate has a diameter of from about 1 micrometers to about 1000 micrometers.

5. The material according to claim 4, wherein said substrate has a diameter of from about 50 micrometers to about 500 micrometers.

6. The material according to claim 1, wherein said metal ilm is a member selected from the group consisting of mickel film, copper film, silver film, gold film, platinum film, palladium film and combinations thereof.

7. The material according to claim 6, wherein said metal film is a gold film.

8. The material according to claim 1, wherein said organic layer comprises a plurality of components, each component comprising a moiety which associates with said metal film.

9. The material according to claim 8, wherein said moiety associates with said metal film through a mechanism which is a member selected from the group consisting of covalent bonding, ionic bonding, coordination, van der Waals interactions, chemisorption, physisorption and combinations thereof.

10. The material according to claim 1, wherein said organic layer comprises an organosulfur moiety.

11. The material according to claim 10, wherein said organic layer comprises a group having the structure:

wherein
R$^1$ is a linking group between sulfur and X$^1$;
X$^1$ is a member selected from the group consisting of H, halogen, recognition moieties, hydrophilic polymers and combinations thereof;
n is a number between 1 and 50.

12. The material according to claim 11, wherein R$^1$ is a member selected from the group consisting of stable linking groups and cleaveable linking groups.

13. The material according to claim 12, wherein R$^1$ is a stable linking group which is a member selected from the group consisting of alkyl, substituted alkyl, aryl, arylalkyl, substituted aryl, substituted arylalkyl, saturated cyclic hydrocarbon, unsaturated cyclic hydrocarbon, heteroaryl, heteroarylalkyl, substituted heteroaryl, substituted heteroarylalkyl, hetcrocyclic, substituted heterocyclic and heterocyclicalkyl groups.

14. The material according to claim 13, wherein R$^1$ is a member selected from the group consisting of alkyl and substituted alkyl groups.

15. The material according to claim 12, wherein R$^1$ is a cleaveable linking group comprising a cleaveable moiety which is a member selected from group consisting of disulfide, ester, imide, carbonate, nitrobenzyl, phenacyl and benzoin groups.

16. The material according to claim 10, wherein said organic layer comprises:

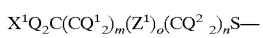

wherein,
X$^1$ is a member selected from the group consisting of halogen and recognition moieties;
Q, Q$^1$ and Q$^2$ are independently members selected from the group consisting of H and halogen;
Z$^1$ is a member selected from the group consisting of —CQ$_2$—, —CQ$^1_2$—, —CQ$^2_2$—, —O—, —S—, —NR$^1$—, —C(O)NR$^1$ and R$^1$NC(O)—,
in which;
R$^1$ is a member selected from the group consisting of H, alkyl, substituted alkyl, aryl, substituted aryl, heteroaryl and heterocyclic groups;
m is a number between 0 and 40; and
n is a number between 0 and 40.
o is a number between 0 and 5.

17. The material according to claim 16, wherein Q, Q$^1$ and Q$^2$ are independently members selected from the group consisting of H and fluorine.

18. The material according to claim 11, wherein said organic layer comprises:

$R^2OCH_2CH_2(OCH_2CH_2)_u(CH_2)_vS—,$ in which
R$^2$ is a member selected from the group consisting of H, alkyl, acyl and recognition moieties;
u is a number between 1 and 50; and
v is a number between 0 and 20.

19. The material according to claim 18, wherein R$^2$ is a member selected from H and CH$_3$.

20. The material according to claim 18, wherein u is a number between 5 and 20.

21. The material according to claim 1, wherein said recognition moiety is a member selected from the group consisting of biomolecules, organic groups, metal chelates and organometallic moieties.

22. The material according to claim 21, wherein said organic group is a member selected from the group consisting of amines, carboxylic acids, drugs, chelating agents, crown ethers, cyclodextrins and combinations thereof.

23. The material according to claim 21, wherein said biomolecule is a member selected from the group consisting of antibodies, antigens, carbohydrates, nucleic acids, peptides, enzymes and receptors.

24. A method of producing a multilayered particle comprising:
(a) contacting a particulate substrate with a metal plating solution to form a particle having a metal film essentially completely coating said particle;
(b) contacting said particle from step (a) with a solution complising nitric acid, thereby activating said metal film;
(c) contacting said particle from step (b) with a plurality of organic molecules that associate with the activated metal film, thereby forming an organic layer on said particle.

25. The material according to claim 24, wherein said metal film is a member selected from the group consisting of nickel film, copper film, silver film, gold film, platinum film, palladium film and combinations thereof.

26. The method according to claim 24, further comprising, prior to step (a), contacting a particulate substrate with a sensitizer to form a sensitized particulate substrate.

27. The method according to claim 26, further comprising, prior to step (a), contacting said sensitized particulate substrate with a silver solution to form a silver coated particle.

28. The method according to claim 27, wherein said silver solution comprises AgNO$_3$.

29. The method according to claim 27, wherein said silver solution further comprises ammonia.

30. The method according to claim 26, wherein said sensitizer is a transition metal salt.

31. The method according to claim 30, wherein said transition metal salt is a salt of Sn$^{+2}$.

32. The method according to claim 24, wherein said particulate substrate is a member selected from silica particles, alumina particles and carbohydrate particles.

33. The method according to claim 24, wherein said gold plating solution comprises a reducible gold salt.

34. The method according to claim 33, wherein said gold plating solution further comprises a reducing agent.

35. The method according to claim 33, wherein said reducible gold salt is Na$_3$Au(SO$_3$)$_2$.

36. The method according to claim 33, wherein said reducing agent is formaldehyde.

37. The method according to claim 24, wherein said plurality of organic molecules comprises an organosulfur.

38. The method according to claim 24, wherein said plurality of organic molecules comprises a moiety selected from the group consisting of recognition moieties, reactive moieties, protected reactive moieties and combinations thereof.

39. The method according to claim 38, wherein said plurality of organic molecules comprises a reactive moiety and said method further comprises:
(d) reacting said reactive moiety with a recognition moiety.

40. The method according to claim 38, wherein said plurality of organic molecules comprises a protected reactive moiety and said method further comprises:
(d) deprotecting said protected reactive moiety to form a reactive moiety;
(e) reacting said re active moiety with a recognition moiety.

41. The method according to claim 24, wherein said organic layer comprises:

$X^1Q_2C(CQ^1_2)_m(Z^1)_o(CQ^2_2)_nS—$ wherein,
X$^1$ is a member selected from the group consisting of halogen, drugs, chelating agents, crown ethers, cyclodextrins, antibodies, antigens, carbohydrates, nucleic acids, peptides, enzymes, receptors and combinations thereof;
Q, Q$^1$ and Q$^2$ are independently members selected from the group consisting of H and halogen;
Z$^1$ is a member selected from the group consisting of —CQ$_2$—, —CQ$^1_2$—, —CQ$^2_2$—, —O—, —S—, —NR$^1$—, —C(O)NR$^1$ and R$^1$NC(O)—,
in which;
R$^1$ is a member selected from the group consisting of H, alkyl, substituted alkyl, aryl, substituted aryl, heteroaryl and heterocyclic groups;
m is a number from 0 to 40;
n is a number from 0 to 40;
o is a number from 0 to 5.

42. A multilayered material comprising:
a particulate substrate;
a metal film essentially completely coating said substrate, applied to said substrate by electroless deposition; and
an organic layer attached to said metal film, comprising;

$X^1 Q_2C(CQ^1_2)_m(Z^1)_o(CQ^2_2)_nS—$ wherein,
X$^1$ is a member selected from the group consisting of halogen, drugs, chelating agents, crown ethers, cyclodextrins, antibodies, antigens, carbohydrates, nucleic acids, peptides, enzymes, receptors and combinations thereof;
Q, Q$^1$ and Q$^2$ are independently members selected from the group consisting of H and halogen;
Z$^1$ is a member selected from the group consisting of —CQ$_2$—, —CQ$^1_2$—, —CQ$^2_2$—, —O—, —S—, —NR—, —C(O)NR$^1$ and R$^1$NC(O)—,
in which;
R$^1$ is a member selected from the group consisting of H, alkyl, substituted alkyl, aryl, substituted aryl, heteroaryl and heterocyclic groups;
m is a number from 0 to 40;
n is a number from 0 to 40; and
o is a number from 0 to 5.

43. A multilayered material comprising:
a particulate substrate;
a metal film essentially completely coating said substrate, applied to said substrate by electroless deposition; and
an organic layer attached to said metal film, comprising;

$$R^2OCH_2CH_2(OCH_2CH_2)_u(CH_2)_vS-$$

wherein,
$R^2$ is a member selected from the group consisting of H, alkyl, acyl and recognition moieties;
u is a number from 1 to 50; and
v is a number from 0 to 20.

44. The multilayered material according to claim 43, wherein said recognition moiety is a member selected from the group consisting of halogen, drugs, chelating agents, crown ethers, cyclodextrins, antibodies, antigens, carbohydrates, nucleic acids, peptides, enzymes, receptors and combinations thereof.

* * * * *